United States Patent
Trinh et al.

(10) Patent No.: US 6,287,550 B1
(45) Date of Patent: Sep. 11, 2001

(54) ANIMAL CARE SYSTEM AND LITTER WITH REDUCED MALODOR IMPRESSION

(75) Inventors: Toan Trinh, Maineville; Helen Bernardo Tordil; Alex Haejoon Chung, both of West Chester; George Joseph Harvey, Fairfield; Zaiyou Liu, West Chester; Leslie A. Mowry, Wyoming, all of OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 09/331,247

(22) PCT Filed: Dec. 17, 1997

(86) PCT No.: PCT/US97/23702

§ 371 Date: Jul. 9, 1999

§ 102(e) Date: Jul. 9, 1999

(87) PCT Pub. No.: WO98/27261

PCT Pub. Date: Jun. 25, 1998

Related U.S. Application Data

(60) Provisional application No. 60/032,752, filed on Dec. 17, 1996, provisional application No. 60/033,650, filed on Dec. 17, 1996, provisional application No. 60/033,651, filed on Dec. 17, 1996, provisional application No. 60/033,022, filed on Dec. 17, 1996, and provisional application No. 60/033,648, filed on Dec. 17, 1996.

(51) Int. Cl.$^7$ .............................. A61L 11/00; A61L 9/04; A61L 9/00

(52) U.S. Cl. ................. 424/76.6; 424/45; 424/76.1; 424/76.4; 119/171; 119/173

(58) Field of Search ........................... 424/45, 76.1, 76.4, 424/76.6; 119/171, 173

(56) References Cited

U.S. PATENT DOCUMENTS

| | | | |
|---|---|---|---|
| 4,494,481 | * 1/1985 | Rodriguez et al. | ................. 119/1 |
| 4,622,221 | * 11/1986 | Schleppnik | ...................... 424/76 |
| 4,883,021 | * 11/1989 | Ducharme et al. | .................. 119/1 |
| 4,949,672 | 8/1990 | Ratcliff et al. | ........................ 119/1 |
| 5,154,594 | * 10/1992 | Gamlen | ............................ 119/171 |

FOREIGN PATENT DOCUMENTS

| | | | |
|---|---|---|---|
| G9308295.9 | 9/1993 | (DE) | ............................. A01K/23/00 |
| 0 109 276 A2 | 5/1984 | (EP) | ............................. A01K/1/015 |
| 0 242 683 A2 | 10/1987 | (EP) | ............................. A01K/1/015 |
| 0 410 576 A1 | 1/1991 | (EP) | ............................. A01K/1/015 |
| 2 629 678 | 4/1988 | (FR) | ............................. A01K/1/15 |
| WO 89/02698 | 4/1989 | (WO) | ............................. A01K/1/015 |
| 96/04940 | * 2/1996 | (WO) | . |
| WO 96/04940 | 2/1996 | (WO) | ............................. A61L/9/01 |

\* cited by examiner

*Primary Examiner*—Thurman K. Page
*Assistant Examiner*—S. Tran
(74) *Attorney, Agent, or Firm*—Jason J. Camp; Frank C. Turner

(57) ABSTRACT

Animal care systems desirably include animal litter with reduced malodor impression comprising solid moisture-absorbing material and effective amounts of both odor absorbing material, preferably, cyclodextrin, or derivative thereof, and material for reducing the formation of malodor, e.g., antibacterial and/or urease inhibitor, preferably water-soluble metallic salt such as zinc salt. Behavior control products are also provided including animal repellent and attractant products, preferably in spray containers, and freshening and cleaning products, also especially in spray containers, and, preferably, in association with instructions for using the products to carry out a method of animal control in which the animal litter is refreshed as needed, and areas are treated with repellent and attractant products to influence the animals to avoid certain areas and frequent other areas, and products for cleaning areas where accidents occur and discouraging the animal from returning to those areas.

85 Claims, No Drawings

ANIMAL CARE SYSTEM AND LITTER WITH REDUCED MALODOR IMPRESSION

This application is a 371 of PCT/US97/23702 filed Dec. 17, 1997, this application claims benefit of provisional application 60/032,752 and provisional application 60/033,650 Dec. 17, 1996 and provisional application 06/033,651 Dec. 17, 1996 and provisional application 60/033,022 Dec. 17, 1996 and provisional application 06/033,648 Dec. 17, 1996.

TECHNICAL FIELD

The present invention relates to animal litter with reduced malodor impression comprising both odor absorbent preferably, cyclodextrin, or derivative thereof, and material for reducing the formation of malodor, preferably water-soluble metallic salt. It also relates to the preparation of the animal litter and compositions designed to augment the malodor reduction during use. It also relates to the use of various odors to control the behavior of animals, especially cats.

BACKGROUND OF THE INVENTION

The control of odor in animal litter has been a continuing problem. Suggested solutions include the use of bacteriostats such as: halogenated aromatic hydrocarbons (U.S. Pat. No. 4,494,482, Arnold, issued Jan. 22, 1985); soluble salts of transition metals of Group Ib or Group IIb of the periodic table of elements, especially zinc, which are taught as both bacteriostats and urease inhibitors (U.S. Pat. No. 4,494,481, Rodriguez et al., issued Jan. 22, 1985 and U.S. Pat. No. 4,736,706, Lang, issued Apr. 12, 1988); boron containing compounds which are claimed to be urease inhibitors (U.S. Pat. Nos. 4,949,672 and 5,176,108, Ratcliff et al. and Jenkins et al., issued Aug. 21, 1990 and Jan. 5, 1993 respectively); sodium bisulfite complexes (U.S. Pat. No. 5,267,531, Appel et al., issued Dec. 7, 1993); and sodium or potassium bicarbonate (U.S. Pat. Nos. 5,303,676 and 5,421,291, Lawson and Lawson et al., issued Apr. 19, 1994 and Jun. 6, 1995 respectively). Other approaches to controlling odor include the use of absorbents for odor such as cyclodextrin and polycarboxylate polymers (U.S. Pat. Nos. 4,727,824; 4,844,010; 4,881,490; and 4,883,021, Ducharme et al., issued Mar. 1, 1988; Jul. 4, 1989; Nov. 21, 1989; and Nov. 28, 1989 respectively).

Still another approach of "covering up" the bad odor involves using encapsulated perfiumes (U.S. Pat. No. 4,407,231, Colbom et al. issued Oct. 4, 1983). Thus, many commercial cat litter products contain a fragrance to mask the malodor and to provide a freshness impression. Many of these fragrances are developed with human aesthetic preference in mind, apparently without consideration of the effect to the animal Thus, many perfumes used in commercial cat litter compositions contain significant amounts of ingredients that are repulsive to cats. On the other hand, commercially available products which claim control of animal behavior, such as cat repellent and cat attractant products, contain only the purported active ingredients without consideration to human aesthetics.

Many types of materials are used as animal litter. Clay and various cellulosic materials are commonly used, as disclosed in the above patents and additional disclosures of materials that can be used are found in U.S. Pat. Nos.: 5,064,407, Peiffer, issued Nov. 12, 1991; U.S. Pat. No. 5,100,600, Keller et al., issued Mar. 31, 1992; U.S. Pat. No. 5,207,389, Hall et al., issued May 4, 1993; U.S. Pat. No. 5,209,186, Dewing, issued May 11, 1993; and U.S. Pat. No. 5,229,348, Ivie, issued Jul. 20, 1993. Preferred animal litter materials are those that "clump" to permit ready removal of the material that has been contacted by, e.g., urine and/or feces. such as U.S. Pats. Re. No. 33,983, Hughes, issued Jul. 7, 1992 and U.S. Pat. No. 5,193,489, Hardin, issued Mar. 16, 1993. All of the above patents are incorporated herein by reference.

SUMMARY OF THE INVENTION

A pet control system is provided, optionally, but preferably comprising a solid liquid-absorbing litter material, e.g., one that is useful as animal litter, containing both an effective amount of material that inhibits the formation of odor that has at least one attribute selected from the group consisting of antimicrobial activity, urease inhibition activity, pH adjustment activity, and mixtures thereof, and also, an effective amount of odor absorbing material for objectionable odor molecules, said odor absorbing material preferably being selected from the group consisting of cyclodextrin; zeolites; activated carbon; acidic, salt-forming materials; and mixtures thereof. Preferably, the combination does not include both bicarbonate and zinc oxide, as discussed hereinafter. The term "animal litter" comprises litter for birds, etc., and any other species that creates a soil that contains urea or any other material that decomposes to form malodors. The system also optionally, but preferably, comprises providing odorants that attract and/or repel pets, while at the same time are pleasant to humans, so that the pet owner can influence the behavior of the pet to benefit both the pet and the owner. Such odorants are optionally, but preferably, provided in multiple forms, including, optionally, but preferably, either complexed, or chemically altered, so as to provide timed presentation of the odorants, and/or optionally, but preferably, in a form that allows them to be distributed, e.g., as in a spray, to create, augment, and/or sustain the desired effect, as disclosed hereinafter.

A desirable way to control objectionable odor in animal litter is to inhibit its formation. However, even the most effective inhibitors of odor formation cannot totally prevent formation of malodor and some malodor is associated with the excretions of animals. Furthermore, for many materials, the levels required for total prevention create health risks. Therefore, the most effective, and safest, way to control objectionable odor in animal litter is to combine inhibition with absorbence of the malodor that is produced.

The preferred combination is a mixture of zinc compound that provides zinc ions to inhibit odor formation and cyclodextrins or their derivatives, especially β-cyclodextrin and/or its derivatives, to absorb the odor that is created.

DETAILED DESCRIPTION OF THE INVENTION

(I) The Animal Litter

The animal litter is a highly desirable part of the pet control system. It is used for its normal purpose, i.e., to control the undesirable odors created by the natural excretions of the pet. The animal litter herein comprises: (A) solid liquid-absorbing litter material; (B) an effective amount of material that inhibits the formation of odor that preferably has at least one attribute selected from the group consisting of antimicrobial activity, urease inhibition activity, pH adjustment activity, proteolytic activity, and mixtures thereof; and (C) materials for absorbing the undesirable odors, all of the above ingredients being present in effective amounts to provide the desired effects.

(A) THE SOLID LIQUID-ABSORBING LITTER MATERIAL

Any solid liquid (moisture) absorbing material suitable for use, e.g., as an animal litter is suitable for use in the present invention. Suitable examples include minerals, typically clay such as kaolinites, montmorillonites, or bentonites; fly ash as obtained from the burning of coal; but also absorbing fibrous materials or webs, like paper, cellulosic webs, or polymeric fibrous webs; wood chips; alfalfa; bark; straw; sand; pelletized absorbing litter materials (e.g. sawdust or polyurethane foam); and the like, including mixtures thereof. Other examples of suitable solid absorbing litter materials are disclosed in U.S. Pat. No. 3,921,581, issued Nov. 25, 1975 to Brewer, incorporated herein by reference.

In one absorbent composition, there is a major amount of a cellulosic material, e.g., a cereal or grain hull, or peanut hulls, along or preferably in admixture with, a second cellulose material comprised of plant pulp, either vegetable or fruit pulp. The cellulosic material, hulls and pulp are ground to a desirable particle size and admixed with a minor amount of a suitable binder, up to about 20% by weight. Suitable binders are the carbohydrates, protein or mixtures thereof, such as flour and starch from plant sources, and the synthetic binders disclosed hereinafter. The cellulosic hull materials will generally be obtained from cereal grain sources such as corn, rice, wheat, oats and the like, soybean, sunflower and cotton seeds or peanut hulls. The plant pulp materials are generally obtained from vegetable sources such as beets, tomato, apple, grape or citrus pulp generally obtained for citrus fruits such as oranges, lemon, lime, grapefruit and the like. The carbohydrate binders are generally flours and starches from cereal grains such as corn, rice, wheat, oats and the like. Protein such as gluten found in wheat flour, or protein from bean or seed sources such as soybean or flaxseed and the like also provide suitable binders.

Other materials that can be used for litters include clay or clay-like materials. Their ability to absorb, or adsorb, moisture makes them excellent candidates for litters. Suitable litters include specific clays such as Georgia White clay, attapulgite, bentonite, kaolinite, halloysite, montmorillonite, smectite, vermiculite, hectorite, diatomaceous earth, Fuller's earth, fossilized plant materials, expanded perlites, gypsum and other equivalent litter materials known to those skilled in the art. Preferred clays are those having water expanding crystal lattices, such as bentonite, i.e., montmorillonite. The clay particles can be comminuted. That is, they are pelletized or formed into particles which have a size varying from about 200 mesh USS (0.075 mm) to about 3½ mesh (5.6 mm), preferably from about 60 mesh (0.25 mm) to about 4 mesh (4.75 mm).

A desirable property, which is characteristic of certain natural earths which may be used as litter, is the tendency to "clump". Clumping is a tendency, marked in certain earths and less marked or absent in others, for the earth particles to adhere firmly to each other when wet to form a mass having sufficient physical integrity to enable it to be removed from the remainder of the particles without undue crumbling or loss of peripheral litter material. The liquid with which the litter has been wet is entrained in the clump and is removed with it. Where the earth has good clumping properties substantially all of the liquid can be retained in the clump and the portion of the earth which remains after the removal of the clump can be completely dry. This property provides a means for removing urine from used litter which, in conjunction with the physical removal of feces, results in a residue of relatively uncontaminated litter, with diminished levels of undesired odors. The litter can then be replenished with fresh litter. This represents an economical use of litter in comparison with the complete replenishment of the litter.

The present invention is especially good when the litter has clumping properties, which further limits the amount of odor that is created. If the litter has only poor or medium clumping properties, or if better clumping is required, one can use techniques such as are found in U.S. Pat. No. 5,193,489. The litter can be an earth, for example, such as a montmorillonite or other smectite, suitably in the alkaline earth metal form, an attapulgite, a palygorskite or a sepiolite. U.S. Pat. No. 5,014,650 relates to litter comprising a porous, inert solid substrate, such as a clay, containing a cellulosic ether in an amount sufficient to agglomerate the animal urine deposited on the litter to form a gelled agglomerate having sufficient mechanical integrity to be conveyed from the litter box as a discrete entity. Additional polymers disclosed to be useful in the litter include polyvinyl alcohol, xanthan gum, gum acacia and various water-soluble polysaccharides. U.S. Pat. No. 4,676,196 describes an absorbing non-clay litter material comprising a mix of particulate litter materials which are caused to agglomerate to form non-compacted particles of a required size by tumbling in the presence of a moistened binder comprising starches, gums such as guar gum or glues. The '489 patent provides an animal litter comprising a particulate earth substrate in admixture with a water soluble or dispersible polysaccharide selected from the galactomannan gums, said polysaccharide being present in an amount sufficient to increase the inherent clumping ability of the earth. A galactomannan is a polysaccharide mainly or wholly consisting of mannose and galactose, and preferably comprising a chain of mannose units bearing galactose side-chains. It is alleged that the galactomannans can be selected to be effective at relatively low concentrations and to give a fast clumping response. Vegetable based gums are usually marketed in a number of grades ranging from the relatively impure base gum, through purified gums from which some extraneous vegetable matter has been removed to derivatised gums which have been treated chemically to alter their characteristics in some way. The '489 patent teaches that the gums are preferably relatively purified and can be derivatised, e.g. by reaction with propylene oxide to form the hydroxy propyl ether, to augment their hydrophilic character so as to be particularly effective. The gum can also be treated to reduce its alkalinity in aqueous dispersion or solution e.g. by the inclusion therein of a relatively weak organic or inorganic acid for example one having a pK value in aqueous solution of at least 4.0.

Preferred galactomannan gums are guar gum or derivative thereof. The concentrations of cellulose ethers specifically disclosed to be effective in U.S. Pat. No. 5,014,650 range from 0.3% upwards with some failures at 0.5% by weight. The galactomannans used according to the '489 patent are alleged to give effective clumping at concentrations down to 0.05% by weight of the earth (dry weight) or below in certain instances and are preferably used in from 0.02% to 1% by weight although any larger quantities, for example up to 2.5% or more by weight. Such litters are mixed with particles of the polysaccharide. The earth preferably has a particle size mainly, for example at least 95% by weight, in the range of about 10 mesh (1.7 mm) to 140 mesh (0.11 mm), preferably about 18 mesh (1 mm) to about 100 mesh (0.15 mm). The polysaccharide preferably has a similar size range. The presence of the polysaccharide in particulate form is alleged to encourage swift dissolution or dispersion in liquid, in comparison with gum which might have been deposited onto the earth particles from solution, and therefore to encourage a quick clumping response. Pellitized litter materials (e.g., sawdust or polyurethane foam) typically have particle sizes in the range from about 1 mm to about 1.3 cm, preferably from about 2.5 mm to about 1 cm.

The basic litter material can be any of the art recognized materials, with those that have the ability to clump being preferred.

(B) MATERIALS TO INHIBIT FORMATION OF ODOR, ESPECIALLY ANTIMICROBIALS AND/OR UREASE INHIBITORS

The litter contains an effective amount of material to inhibit the formation of undesirable odors, typically comprising urease inhibitor and/or antimicrobial.

Metallic Salts

The animal litter products of the present invention are prepared by contacting the solid absorbing litter material with, preferably, an aqueous solution of the antimicrobial and/or urease inhibitor, preferably transition metal ion. Suitable sources of the transition metal ions are their soluble salts. The preferred salts are silver, copper, zinc, ferric, and aluminum salts, more preferably zinc. It is also desirable that the anion provide some benefit. E.g., the anion can have the ability to provide urease inhibition, such as borate, phytate, etc. Suitable examples are silver chlorate, silver nitrate, mercury acetate, mercury chloride, mercury nitrate, copper metaborate, copper bromate, copper bromide, copper chloride, copper dichromate, copper nitrate, copper salicylate, copper sulfate, zinc acetate, zinc borate, zinc phytate, zinc bromate, zinc bromide, zinc chlorate, zinc chloride, zinc sulfate, cadmium acetate, cadmium borate, cadmium bromide, cadmium chlorate, cadmium chloride, cadmium formate, cadmium iodate, cadmium iodide, cadmium permanganate, cadmium nitrate, cadmium sulfate, and gold chloride. Other salts that have been disclosed as having urease inhibition properties include ferric and aluminum salts, especially the nitrates, and bismuth salts. Zinc salts are preferred.

Silver salts and mercury salts are very effective but are also toxic and expensive and are therefore used at levels ranging from about 50 ppm to about 500 ppm, preferably from about 100 ppm to about 300 ppm. Copper salts, zinc salts and cadmium salts are most effectively used at levels ranging from about 500 ppm to about 7500 ppm, preferably at levels from about 1000 ppm to about 4000 ppm, more preferably from about 1500 ppm to about 2500 ppm. Gold salts are effective and substantially less toxic than silver or mercury. However, it is doubtful that the use of gold salts would ever be economically feasible.

The preferred metallic salt, preferably water-soluble zinc salts, can be added to the solution used to prepare the litter of the present invention. A water-soluble metallic salt can be used as an odor control agent. A water-soluble metallic salt can be present in the freshening composition of the present invention to absorb amine and sulfur-containing compounds. Furthermore, they usually do not contribute an odor of their own. Preferably the water-soluble metallic salts are selected from the group consisting of copper salts, zinc salts, and mixtures thereof.

The preferred zinc salts have been used most often for their ability to ameliorate malodor, e.g., in mouth wash products, as disclosed in U.S. Pat. No. 4,325,939, issued Apr. 20, 1982 and U.S. Pat. No. 4,469,674, issued Sep. 4, 1983, to N. B. Shah, et al., incorporated herein by reference. U.S. Pat. No. 3,172,817, issued to Leupold, et al., discloses deodorizing compositions containing slightly water-soluble salts of an acyl-acetone with a polyvalent metal, including copper and zinc salts. Said patents are incorporated herein by reference. The zinc salts are preferably water soluble, and therefore the solutions herein should not be so alkaline so as to avoid formation of zinc oxide, which is much less soluble.

Examples of preferred water-soluble zinc salts are zinc chloride, zinc gluconate, zinc lactate, zinc maleate, zinc salicylate, zinc sulfate, etc. Highly-ionized and soluble zinc salts such as zinc chloride, provide the best source of zinc ions. Examples of preferred copper salts are copper chloride and copper gluconate. Preferred metallic salts are zinc chloride and copper chloride.

Metallic salts are added to the litter composition of the present invention typically at a level of from about 0.001% to about 2%, preferably from about 0.01% to about 1%, more preferably from about 0.05% to about 0.5%, by weight of the litter composition. When zinc salts are used as the metallic salt, it is preferable that the pH of the solution is adjusted to less than about 7, more preferably less than about 6, most preferably, less than about 5, in order to keep the solution clear.

Urease Inhibitors

There are many materials that exhibit urease inhibition and/or suppression. A partial list of materials that have been disclosed as inhibitors includes the metallic salts listed above; hydroxamic acid, modified hydroxamic and/or dihydroxyamic acids, e.g., substituted with various hydrocarbon groups such as acyl, e.g., aceto-, chloronitrobenzamidoaceto-, and nitrobenzamidoaceto- (e.g., 2-para), $C_{1-21}$ alkyl, aryl, and/or alkaryl groups, cycloalkyl (e.g., cyclohexyl), peptidyl, naphthyloxy-alkane, and their salts; thiourea; hydroxylamine; salts of phytic acid, especially sodium, potassium, calcium, and magnesium; extracts of plants of various species, including various tannins, e.g. carob tannin, and their derivatives such as chlorogenic acid derivatives; naturally occurring acids such as ascorbic acid, citric acid, and their salts; phenyl phosphoro diamidate/diamino phosphoric acid phenyl ester; metal aryl phosphoramidate complexes, including substituted phosphorodiamidate compounds; phosphoramidates without substitution on the nitrogen; boric acid and/or its salts, including especially, borax, and/or organic boron acid compounds; the compounds disclosed in European Patent Application 408,199, incorporated by reference; sodium, copper, manganese, and/or zinc dithiocarbamate; quinones; phenols; thiurams; substituted rhodanine acetic acids; alkylated benzoquinones; formamidine disulphide; 1:3-diketones maleic anhydride; succinamide; phthalic anhydride; pehenic acid; N,N-dihalo-2-imidazolidinones; N-halo-2-oxazolidinones; thio- and/or acyl-phosphoryltriamide and/or substituted derivatives thereof; thiopyridine-N-oxides, thiopyridines, and thiopyrimidines; oxidized sulfur derivatives of diaminophosphinyl compounds; cyclotriphosphazatriene derivatives; ortho-diaminophosphinyl derivatives of oximes; bromo-nitro compounds; S-aryl and/or alkyl diamidophosphorothiolates; diaminophosphinyl derivatives; mono- and/or poly-phosphorodiamide; 5-substituted-benzoxathiol-2-ones; N-(diarninophosphinyl)arylcarboxamides; alkoxy-1,2-benzothaizin compounds; etc.

As stated above, a large number of urease inhibitors are known, some having been purposefully synthesized by the pharmaceutical industry, and others whose original use was for purposes outside the realm of urease inhibition, but which can also be suitably employed to act as structural mimics of urea. These latter compounds include low molecular weight, water soluble materials which act as an irreversible substrate or modifier of the active site of the urease enzyme.

Among the low molecular weight urease inhibitors that are thought to serve as substrate mimics are hydroxamic acid and the substituted hydroxamic acids mentioned above. Acetohydroxamic and propiohydroxamic acid are the most common of the acyl substituted hydroxamic acids. These two compounds, as well as the parent hydroxamic acid and the alkali or alkaline earth salts of said acids, are particularly efficacious in inhibiting urease enzyme activity in vitro.

A variety of phosphorus compounds, including those disclosed hereinbefore, have been prepared for in vivo reduction in urease activity. Many of the pharmaceutical industry generated products are compatible with the environment due to their bio-degradability and the structure and oxidation state of the phosphorus containing moiety.

In particular, phosphorus triamides of the general formula:

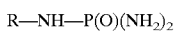

R—NH—P(O)(NH$_2$)$_2$ wherein R is hydrogen, phenyl, substituted phenyl, alkyl, alkenyl, and other suitable moieties or preferably N-(diaminophosphinyl)arylcarboxamides of the formula:

R—C(O)—NH—P(O)(NH$_2$)$_2$ wherein R is 3-pyridyl, 2-furanyl, 2-naphthyl, cinnamenyl, benzyl, phenyl, and substituted phenyl are efficacious as urease inhibitors when added in a sufficient amount to inhibit the enzyme urease.

Other preferred urease inhibitors have the general formula:

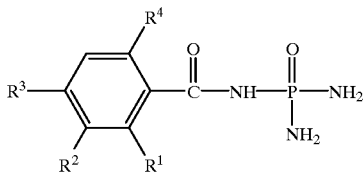

where $R^1$, $R^2$, $R^3$, and $R^4$ is more preferably hydrogen, nitro, halogen, amino, $C_{1-4}$ alkyl, $C_{1-4}$ alkoxy, trifluormethyl, cyano, phenoxy, phenyl, and mixtures thereof. A further embodiment of the present invention includes urease inhibitors of the general formula:

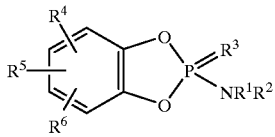

wherein;

$R^1$ and $R^2$ are the same or different and are hydrogen or alkyl having from 1 to about 4 carbon atoms;

$R^3$ is oxygen or sulfur; and $R^4$, $R^5$ and $R^6$ are the same or different and are hydrogen, alkyl, arylamino, diarylamino, halogen, hydroxy, mercapto, alkylmercapto, alkyl mercapto, O-diaminophosphinyl, S-diaminophosphinyl, N-diaminophosphinyl, diaminophosphonyl, amino, cyano, nitro, alkylamino, dialkylamino, arylmercapto, isocyano, isocyanato, trihalomethyl, alkoxy, thiocyano, alkanoyl, or any two $R^4$, $R^5$ and $R^6$ group taken together may form an alkylene or alkenylene chain which may optionally include one or more divalent oxygen, nitrogen, or sulfur moieties forming a 3,4,5 or 6 membered fused ring structure.

A variety of nitrogen containing compounds have been prepared for in vivo use against urease activity. These materials are effective urease inhibitors when used in vivo in the present invention.

The present invention also relates to a composition and method of inhibiting urease activity comprising an effective amount of one or more oxime compounds having the formula

R$^1$—(NR$^6$)$_i$—C(M)—C(NOR$^3$)—R$^2$ wherein $R^1$ and $R^2$ are independently selected from the group consisting of alkyl, aryl, and heteroaryl, or $R^1$ and $R^2$ may be covalently bonded together to form a cyclic alkyl; M is selected from the group consisting of =O, =S, —SR$^4$ and —OR$^4$ (when M is —OR$^4$ or —SR$^4$, there is a hydrogen bonded to the carbon to which M is bonded and $R^4$ is selected from the group consisting of hydrogen, alkyl, aryl and heteroaryl); $R^3$ is selected from the group consisting of hydrogen, alkyl, aryl and heteroaryl; $R^6$ is selected from the group consisting of hydrogen, alkyl, aryl and heteroaryl; and i is selected from the group consisting of 1 and 0.

When $R^1$ is aryl, it is preferably selected from substituted and unsubstituted, preferably 2-furanyl, 3-furanyl, 2-thienyl, 2-pyrrolyl, 3-pyrrolyl and phenyl. Also preferred are these aryl substituted with $C_1$–$C_6$ alkyl, $C_1$–$C_6$ alkoxy, amino, halogen, hydroxy, mercapto, alkyl mercapto, O-diaminophosphinyl, S-diamino-phosphinyl, diarninophosphinyl, diaminophosphonyl, cyano, nitro, alkylamino, di-alkylamino, aryl mercapto, isocyanato, trihalomethyl, alkoxy, thiocyano, and alkanoyl. When $R^1$ is alkyl, it is preferably selected from substituted and unsubstituted, preferably unsubstituted $C_1$–$C_{18}$ alkyl, more preferably $C_1$–$C_{12}$ straight chain.

When $R^2$ is aryl, it is preferably selected from substituted and unsubstituted, preferably 2-furanyl, 3-furanyl, 2-thienyl, 3-thienyl, 2-pyrrolyl, 3-pyrrolyl and phenyl. Also preferred are these aryl substituted with $C_1$–$C_6$ alkyl, $C_1$–$C_6$ alkoxy, amino, halogen, hydroxy, mercapto, alkyl mercapto, O-diamino-phosphinyl, S-diarninophosphinyl, diaminophosphinyl, diaminophosphonyl, cyano, nitro, alkylamino, di-alkylamino, aryl mercapto, isocyanato, trihalomethyl, alkoxy, thiocyano, and alkanoyl. When $R^2$ is alkyl, it is preferably selected from substituted and unsubstituted, preferably unsubstituted $C_1$–$C_{18}$ alkyl, more preferably $C_1$–$C_{12}$ straight chain.

When $R^3$ is aryl, it is preferably substituted or unsubstituted phenyl. When $R^3$ is alkyl, it is preferably selected from substituted and unsubstituted, preferably unsubstituted $C_1$–$C_{18}$ alkyl, more preferably $C_1$—$C_{12}$ straight chain. $R^3$ is most preferably hydrogen.

When $R^4$ is aryl, it is preferably substituted or unsubstituted phenyl. When $R^4$ is alkyl, it is preferably selected from substituted and unsubstituted, preferably unsubstituted $C_1$–$C_{18}$ alkyl, more preferably $C_1$–$C_{12}$ straight chain. $R^4$ is most preferably hydrogen.

When $R^6$ is aryl, it is preferably substituted or unsubstituted phenyl. When $R^6$ is alkyl, it is preferably selected from substituted and unsubstituted, preferably unsubstituted $C_1$–$C_{18}$ alkyl, more preferably $C_1$–$C_{12}$ straight chain. $R^6$ is most preferably hydrogen.

Suitable compounds for use in the present invention include syn- and anti-forms or mixtures thereof.

In particular, oximes of the general formula:

wherein R is hydrogen; or R and $R^2$ are the same or different $C_1$–$C_{22}$ alkyl and branched alkyl, $C_1$–$C_{22}$ alkenyl or branched alkenyl; an aryl group substituted with one or more amino; heterocyclic rings, preferably 2-furanyl, substituted 2-furanyl, 3-furanyl, and substituted 3-furanyl wherein the furanyl substituents are one or more alkyl, amino, cyano, nitro, alkylamino, dialkylamino, aryl mercapto, isocyanato, trihalomethyl, alkoxy, thiocyano, alkanoyl and halogen moieties; in the case where two aryl or two heterocyclic rings or one of each are present that contain more than one substituent, for example, when R or $R^2$ each comprise an aryl or heterocyclic ring such as a 2,4-dichlorofuranyl, 2-chloro-4-methylfuranyl, or a tri-substituted heterocyclic moiety such as 3,4,5-trichlorofuranyl; or R and $R^2$ taken together may form an alkylene or alkenylene chain which may optionally include one of more divalent oxygen, nitrogen, or sulfur moieties forming a 3, 4, 5 or six membered fused ring structure; are efficacious as urease inhibitors in a toilet bowl cleaner and flush tank additive when added in an amount sufficient to inhibit the enzyme urease.

In particular, keto oximes of the general formula:

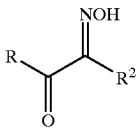

wherein R is hydrogen; or R and $R^2$ are the same or different $C_1$–$C_{22}$ alkyl and branched alkyl, $C_1$–$C_{22}$ alkenyl or branched alkenyl; aryl groups substituted by one or more halogen, hydroxy, mercapto, alkyl mercapto, O-diaminophosphinyl, S-diaminophosphinyl, diaminophosphinyl, diaminophosphonyl, amino, cyano, nitro, alkylamino, dialkylamino, aryl mercapto, isocyanato, trihalomethyl, alkoxy, thiocyano, alkanoyl; or R and $R^2$ taken together may form an alkylene or alkenylene chain which may optionally include one of more divalent oxygen, nitrogen, or sulfur moieties forming a 3, 4, 5 or six membered fused ring structure; R and $R^2$ each comprise a heterocyclic ring, preferably 2-furanyl, substituted 2-furanyl, 3-furanyl, and substituted 3-furanyl; are efficacious as urease inhibitors when added in an amount sufficient to inhibit the enzyme urease. The furanyl substituents can be substituted by one or more alkyl, amino, cyano, nitro, alkylamino, dialkylamino, aryl mercapto, isocyanato, trihalomethyl, alkoxy, thiocyano, alkanoyl and halogen moieties and mixtures thereof. For example, R or $R^2$ may each comprise the same or different di-substituted aryl or heterocyclic moiety such as 2,4-dichlorofuranyl, 2-chloro-4-methylfuranyl, or a tri-substituted moiety such as 2,4,6-trichlorophenyl, or 3,4,5-trichlorofuranyl.

Also surprisingly efficacious as a urease inhibitor when added in an amount sufficient to inhibit the enzyme urease is violuric acid and derivatives of violuric acid having the general formula:

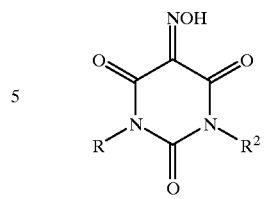

wherein R and $R^2$ can be the same or different and are hydrogen, $C_1$–$C_{22}$ alkyl and branched alkyl, $C_1$–$C_{22}$ alkenyl or branched alkenyl; an aryl or heterocyclic ring substituted by one or more amino, halogen, hydroxy, mercapto, alkyl mercapto, O-diaminophosphinyl, S-diaminophosphinyl, diaminophosphinyl, diaminophosphonyl, cyano, nitro, alkylamino, dialkylamino, aryl mercapto, isocyanato, trihalomethyl, alkoxy, thiocyano, alkanoyl or mixtures thereof.

The urease inhibitor is included in the animal litter composition of the present invention at an effective amount. The term "effective amount" as herein defined means a level sufficient to inhibit or significantly reduce the hydrolysis of urea for a specific period of time. Preferred levels of urea inhibitor are from about 0.0002% to about 5%, more preferably from about 0.002% to about 0.5%. most preferably from about 0.01% to about 0.3%, by weight of the composition.

Antimicrobials

Organic antimicrobials can also be used in the present invention. It is preferable to use a broad spectrum antimicrobial, e.g., one that is effective on both bacteria (both gram positive and gram negative) and fungi. A limited spectrum antimicrobial, e.g., one that is only effective on a single group of microorganisms, e.g., fungi, can be used in combination with a broad spectrum antimicrobial or other limited spectrum antimicrobials with complimentary and/or supplementary activity. A mixture of broad spectrum antimicrobials can also be used.

Antimicrobials useful in the present invention can be biocidal compounds, i.e., substances that kill microorganisms, or biostatic compounds, i.e., substances that inhibit and/or regulate the growth of microorganisms.

Preferred antimicrobials are those that are water-soluble and are effective at low levels because the organic antimicrobials can form inclusion complexes with the preferred cyclodextrin molecules in the treatment solution used to form the animal litter, thus rendering the complexed antimicrobials much less effective. Water-soluble antimicrobials useful in the present invention are those that have a solubility in water of at least about 0.3 g per 100 ml of water, i.e., about 0.3% at room temperature, preferably greater than about 0.5% at room temperature. These types of antimicrobials have a lower affinity to the cyclodextrin cavity, at least in the aqueous phase, and are therefore more available to provide antimicrobial activity. Antimicrobials with a water-solubility of less than about 0.3% and a molecular structure that readily fits into the cyclodextrin cavity, have a greater tendency to form inclusion complexes with the cyclodextrin molecules, thus rendering the antimicrobial less effective to control microbes in the cyclodextrin solution. Therefore, many well known antimicrobials such as short chain alkyl esters of p-hydroxybenzoic acid, commonly known as parabens; N-(4-chlorophenyl)-N'-(3,4-dichlorophenyl) urea, also known as 3,4,4'-trichlorocarbanilide or triclocarban; 2,4,4'-trichloro-2'-hydroxy diphenyl ether, commonly known as triclosan are not preferred in the present invention since they are relatively ineffective when used in conjunction with cyclodextrin. Less water soluble antimicrobial materials can be used, but it is better to apply such materials separately with drying in between the application of the cyclodextrin and the antimicrobial to minimize interaction.

The water-soluble antimicrobial is included in the present invention it is included at an effective amount. The term "effective amount" as herein defined means a level sufficient to prevent growth of microorganisms for a specific period of time. Preferred levels of antimicrobial are from about 0.0001% to about 0.5%, more preferably from about 0.0002% to about 0.2%, most preferably from about 0.0003% to about 0.1% by weight of the composition.

The antimicrobial can be any organic antimicrobial material. Alkyl monocarboxylic acids having from about 3 to about 9 carbon atoms and halogenated aromatic hydrocarbons, e.g., halogenated phenols, halogenated diphenyls and halogenated bis-phenols such as para-chloro-meta-cresol, hexachlorophene, 2,4,4'-trichloro-2'-hydroxydiphenyl ether, trichiorocarbanalide, 2,4-dichloro-meta-xylenol, 3,4,5-tribromosalicylanalide, 3,5,3',4'-tetrachlorosalicylanalide, and mixtures thereof, can be used. Preferred water-soluble antimicrobials include organic sulfur compounds, halogenated compounds, cyclic organic nitrogen compounds, low molecular weight aldehydes, quaternary compounds, dehydroacetic acid, phenyl and phenoxy compounds, and mixtures thereof.

Non-limiting examples of the preferred water-soluble antimicrobials for use in the present invention include a mixture of about 77% 5-chloro-2-methyl-4-isothiazolin-3-one and about 23% 2-methyl-4-isothiazolin-3-one, a broad spectrum antimicrobial available as a 1.5% aqueous solution under the trade name Kathon® CG by Rohm and Haas Co.; 5-bromo-5-nitro-1,3-dioxane, available under the trade name Bronidox L® from Henkel; 2-bromo-2-nitropropane-1,3-diol, available under the trade name Bronopol® from Inolex; 1,1'-hexamethylene bis(5-(p-chlorophenyl) biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N, N'-bis(hydroxy-methyl) urea, commonly known as diazolidinyl urea, available under the trade name Germall II® from Sutton Laboratories, Inc.; N,N''-methylenebis{N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from Sutton Laboratories, Inc.; olymethoxy bicyclic oxazolidine, available under the trade name Nuosept® from Hüls America; formaldehyde; glutaraldehyde; polyaminopropyl biguanide; available under the trade name Cosmocil CQ® from ICI Americas, Inc., or under the trade name Mikrokill® from Brooks, Inc; dehydroacetic acid; and mixtures thereof.

Antimicrobials with a water-solubility of less than about 0.3% and a molecular structure that readily fits into the cyclodextrin cavity, have a greater tendency to form inclusion complexes with the cyclodextrin molecules. Non-limiting examples of such antimicrobials are short chain alkyl esters of p-hydroxyberizoic acid, commonly known as parabens, N-(4-chlorophenyl)-N'-(3,4-dichlorophenyl) urea, also known as 3,4,4'-trichlorocarbanilide or triclocarban; 2,4,4'-trichloro-2'-hydroxy diphenyl ether, commonly known as triclosan. Such poor water soluble antimicrobial materials can be used, but it is better to apply such materials separately (e.g., sprayed as an ethanolic solution) with drying in between the application of the cyclodextrin and the antimicrobial to minimize interaction.

The antimicrobial is included in the animal litter composition of the present invention at an effective amount. The term "effective amount" as herein defined means a level sufficient to prevent growth of microorganisms for a specific period of time. Preferred levels of antimicrobial are from about 0.001% to about 0.3%, more preferably from about 0.003% to about 0.2%, most preferably from about 0.01% to about 0.1%, by weight of the composition.

In general, it is desirable to limit, or exclude, materials that can have adverse effects. Therefore, it is desirable to exclude the more toxic metals and those elements such as boron, that can have adverse effects on the environment (boron can adversely affect citrus crops).

pH Control Materials and Proteases

Other materials that can inhibit the formation of odor include materials with pH activity. Especially useful materials are acidic materials that neutralize the amine molecules that are typically created by bacteria. Polymeric carboxylate materials like polyacrylic acid are useful for this purpose.

Proteases can be useful in preventing odor by digesting excretions in such a way that non-odorous products are created. They can also reduce odor by destroying other enzymes that break down excretions. The typical proteases are disclosed hereinafter as part of the cleaning ingredients used for compositions of type (V).

(C) ODOR ABSORBING MATERIALS

The animal litter products of this invention contain an effective, i.e., odor-absorbing, amount of various odor-absorbing materials. For the purpose of the present invention, the liquid absorbing litter materials, such as clay, saw dust, and the like, are not considered to be odor absorbing materials, except when specifically noted, because the novel development of this invention has the purpose of improving the malodor absorbing/neutralizing capability of the litter compositions which already contain these liquid absorbing litter materials.

Odor-absorbing materials control the undesirable odor by various means to reduce the concentration, or availability, of the malodorous molecules in the ambient air, thus reducing or eliminating the undesirable smell in the air. Such materials include, for example, cyclodextrins, zeolites, activated carbon, kieselguhr, chelating agents, chitin, alkali metal carbonates and bicarbonates, pH buffered materials such as carboxylic acids and the like. Preferred materials are those which absorb primary amines. Materials like the carbonates and bicarbonates that absorb fatty acids are not preferred, and are desirably excluded. Especially preferred are cyclodextrin and/or zeolite. disclosed herein to provide odor control benefits. Some partially neutralized hydrogel-forming odor absorbing gelling materials, such as polyacrylate gelling material and acrylate grafted starch gelling material (vide infra), are also useful in the present invention to control certain ammonia-type odors. These materials also function as fluid absorbing materials.

Zeolite Odor-Absorbing Agent

In general terms, traditional zeolites comprise an aluminate/silicate framework, with associated cations, M, providing overall electrical neutrality. Empirically, the zeolite framework can be represented as

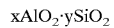

and the electrically neutral zeolite as

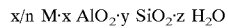

wherein: x and y are each integers, M is a cation and n is the charge on the cation. As noted by the empirical formula, zeolites may also comprise waters of hydration (z H$_2$O). M can be a wide variety of cations, e.g., Na$^+$, K$^+$, NH$_4^+$, alkylammonium, heavy metals, and the like.

A preferred class of zeolites useful in the present invention is characterized as "intermediate" silicate/aluminate zeolites. The "intermediate" zeolites are characterized by SiO$_2$/AlO$_2$ molar ratios of less than about 10. Typically, the molar ratio of SiO$_2$/AlO$_2$ will range from about 2 to about 10. The intermediate zeolites have three advantages over "high" zeolites, disclosed in U.S. Pat. Nos. 4,795,482 and 4,826,497, which are incorporated herein by reference. First, the intermediate zeolites have a higher capacity for amine-type odors which is important for absorbing urine and menses odors. Second, the intermediate zeolites have a larger surface area (about 700–800 m$^2$/g) than high zeolites (about 400 m$^2$/g). Therefore, less intermediate zeolite is needed to absorb a given amount of odor on a weight to weight basis. Third, intermediate zeolites are more moisture tolerant and retain more odor-absorbing capacity in the presence of water.

A wide variety of intermediate zeolites suitable for use herein are commercially available as VALFOR CP301-68, VALFOR 300-63, VALFOR CP300-35 and VALFOR CP300-56, from PQ Corporation, and the CBV100 series (other than Mordenite, as noted below) of zeolites from Conteka.

The zeolites used herein are not of the fibrous type, e.g., various Mordenites, and some types of Y zeolites, since these may be subject to safety issues. Accordingly, the term "zeolite" as used herein is intended to encompass only the non-fibrous zeolites. While some naturally-occurring zeolites meet the objectives of this invention, the synthetic zeolites of the types available in commerce are generally more preferred.

High zeolites are also preferred and can be employed in the practice of this invention either alone or in combination with the intermediate ratio zeolites. High zeolites include, for example, the well-known "molecular sieve" zeolites of the ZSM, beta zeolite, etc., type and the zeolite materials marketed under the trade name ABSCENTS by the Union Carbide Corporation and UOP (See: ABSCENTS, A New Approach for Odor Control by A. J. Gioffre, copyright 1988 by the Union Carbide Corporation). Such materials are preferred over the "intermediate" zeolites for control of odors associated with sulfur compounds, e.g., thiols, mercaptans.

Various other modified zeolite-type materials which can be used in the present invention, such as the manganese-aluminum-phosphorus-silicon-oxide molecular sieves and other zeolite odor-absorbing compositions are described in U.S. Pat. No. 4,793,833, Lok et al.; U.S. Pat. Nos. 4,604,110; 4,437,429; and 4,648,977, which are incorporated herein by reference.

Zeolites typically are present at a level of from about 0.01% g to about 5%, more preferably from about 0.05% to about 2%, by weight of fluid absorbing litter materials disclosed herein, to provide odor control benefits.

Cyclodextrins

The preferred odor absorbing material is uncomplexed cyclodextrin which can be added to the composition of the present invention. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms, therefore this surface is fairly hydrophobic. The unique shape and physical-chemical property of the cavity enable the cyclodextrin molecules to absorb (form inclusion complexes with) organic molecules or parts of organic molecules which can fit into the cavity. Many odor molecules can fit into the cavity.

Non-derivatised (normal) beta-cyclodextrin can be used and is preferred. When non-derivatised beta-cyclodextrin is used to prepare the litter the aqueous solution is preferably heated. A preferred method is to spray an almost saturated aqueous solution of beta-cyclodextrin, preferably heated, e.g., from about 40° C. to about 90° C., preferably from about 50° C. to about 80° C., more preferably from about 60° C. to about 75° C., onto the litter material, preferably with mixing or stirring, to permit a uniform incorporation of as much as possible of the cyclodextrin with the least amount of water.

Another preferred method to apply the beta-cyclodextrin to animal litter material is to spray an aqueous slurry of solid beta-cyclodextrin powder, preferably small particle size beta-cyclodextrin powder, preferably with mixing or stirring, onto the animal litter material. beta-Cyclodextrin powder in the slurry typically has an average particle size of less than about 12 microns, preferably less than about 10 microns, more preferably less than about 8 microns, and even more preferably less than about 5 microns, to provide the best odor control benefit. The particle size is typically between about 0.001 and 10 microns, preferably between about 0.05 and 5 microns. It is highly desirable that at least an effective amount of particles having the said particle sizes. It is desirable that at least about 50%, preferably at least about 65%, more preferably at least about 80%, of the beta-cyclodextrin powder that is present have the said particle sizes.

These small particles of the invention are conveniently prepared by grinding techniques. Cyclodextrin crystals with large particle sizes can be pulverized to obtain the desired smaller particles of less than about 12 microns by using, e.g., a fluid energy mill. In one preferred method, the large beta-cyclodextrin crystals can be pulverized into small particles, then added to water to form the desired slurry. In another preferred method a slurry of large beta-cyclodextrin can be milled to obtain a small particle size slurry. Examples of fluid energy mills are the Trost Air Impact Pulverizers, sold by Garlock Inc., Plastomer Products, Newtown, Pa.; the Micronizer fluid energy mills sold by Sturtevant, Inc., Boston, Mass.; and the Spiral Jet Mill sold by Alpine Division, MicroPul Corporation (Hosokawa Micron International, Inc.), Summit, N.J.

As used herein, the particle size refers to the largest dimension of the particle and to the ultimate (or primary) particles. The size of these primary particles can be directly determined with optical or scanning electron microscopes. The slides must be carefully prepared so that each contains a representative sample of the bulk cyclodextrin powder. The particles sizes can also be measured by any of the other well-known methods, e.g., wet sieving (non-aqueous), sedimentation, light scattering, etc. A convenient instrument that can be used to determine the particle size distribution of the dry powder directly (without having to make a liquid suspension or dispersion) is the Malvern Particle and Droplet Sizer, Model 2600C, sold by Malvern Instruments, Inc., Southborough, Mass. Some caution should be observed in that some of the dry particles may remain agglomerated. The presence of agglomerates can be further determined by microscopic analysis. Some other suitable methods for particle size analysis are described in the article "Selecting a particle size analyzer: Factors to consider," by Michael Pohl, published in Powder and Bulk Engineering, Volume 4 (1990), pp. 26–29, incorporated herein by reference. It is recognized that the very small particles of the invention can readily aggregate to form loose agglomerates that are easily broken apart by either some mechanical action or by the action of water. Accordingly, particles should be measured after they are broken apart, e.g., by agitation or sonication. The method, of course, should be selected to accommodate the particle size and maintain the integrity of the complex particles, with iterative measurements being made if the original method selected proves to be inappropriate.

Other cyclodextrins useful in the present invention are highly water-soluble such as, alpha-cyclodextrin and derivatives thereof, gamma-cyclodextrin and derivatives thereof derivatised beta-cyclodextrins, and/or mixtures thereof. The derivatives of cyclodextrin consist mainly of molecules wherein some of the OH groups are converted to OR groups. Cyclodextrin derivatives include, e.g., those with short chain alkyl groups such as methylated cyclodextrins and ethylated cyclodextrins, wherein R is a methyl or an ethyl group; those with hydroxyalkyl substituted groups, such as hydroxypropyl cyclodextrins and/or hydroxyethyl cyclodextrins, wherein R is a $^-CH_2$—CH(OH)—$CH_3$ or a $^-CH_2CH_2$—OH group; branched cyclodextrins such as maltose-bonded cyclodextrins; cationic cyclodextrins such as those containing 2-hydroxy-3-(dimethylamino)propyl ether, wherein R is $CH_2$—CH(OH)—$CH_2$—$N(CH_3)_2$ which is cationic at low pH; quaternary ammonium, e.g., 2-hydroxy-3-(trimethylarnmonio)propyl ether chloride groups, wherein R is $CH_2$—CH(OH)—$CH_2$—$N^+(CH_3)_3Cl^-$; anionic cyclodextrins such as carboxymethyl cyclodextrins, cyclodextrin sulfates, and cyclodextrin succinylates; amphoteric cyclodextrins such as carboxymethyl/quaternary ammonium cyclodextrins; cyclodextrins wherein at least one glucopyranose unit has a 3-6-anhydro-cyclomalto structure, e.g., the mono-3-6-anhydrocyclodextrins, as disclosed in "Optimal Performances with Minimal Chemical Modification of Cyclodextrins", F. Diedaini-Pilard and B. Perly, The 7th International Cyclodextrin Symposium Abstracts, April 1994, p. 49, herein incorporated by reference; and mixtures thereof. Other cyclodextrin derivatives are disclosed in U.S. Pat. No. 3,426,011, Parrnerter et al., issued Feb. 4, 1969; U.S. Pat. Nos. 3,453,257; 3,453,258; 3,453,259; and 3,453, 260, all in the names of Parmerter et al., and all issued Jul. 1, 1969; U.S. Pat. No. 3,459,731, Gramera et al., issued Aug. 5, 1969; U.S. Pat. No. 3,553,191, Parmerter et al., issued Jan. 5, 1971; U.S. Pat. No. 3,565,887, Parmerter et al., issued Feb. 23, 1971; U.S. Pat. No. 4,535,152, Szejtli et al., issued Aug. 13, 1985; U.S. Pat. No. 4,616,008, Hirai et al., issued Oct. 7, 1986; U.S. Pat. No. 4,678,598, Ogino et al., issued Jul. 7, 1987; U.S. Pat. No. 4,638,058, Brandt et al., issued Jan. 20, 1987; and U.S. Pat. No. 4,746,734, Tsuchiyama et al., issued May 24, 1988; all of said patents being incorporated herein by reference.

Highly water-soluble cyclodextrins are those having water solubility of at least about 10 g in 100 ml of water at room temperature, preferably at least about 20 g in 100 ml of water, more preferably at least about 25 g in 100 ml of water at room temperature. These are easy to use, but are typically more expensive than the non-derivatised beta-cyclodextrin. Examples of preferred water-soluble cyclodextrin derivatives suitable for use herein are hydroxypropyl alpha-cyclodextrin, methylated alpha-cyclodextrin, methylated beta-cyclodextrin, hydroxyethyl beta-cyclodextrin, and hydroxypropyl beta-cyclodextrin. Hydroxyalkyl cyclodextrin derivatives preferably have a degree of substitution of from about 1 to about 14, more preferably from about 1.5 to about 7, wherein the total number of OR groups per cyclodextrin is defined as the degree of substitution. Methylated cyclodextrin derivatives typically have a degree of substitution of from about 1 to about 18, preferably from about 3 to about 16. A known methylated beta-cyclodextrin is heptakis-2,6-di-O-methyl-β-cyclodextrin, commonly known as DIMEB, in which each glucose unit has about 2 methyl groups with a degree of substitution of about 14. A preferred, more commercially available methylated beta-cyclodextrin is a randomly methylated beta-cyclodextrin having a degree of substitution of about 12.6. The preferred cyclodextrins are available, e.g., from Cerestar USA, Inc. and Wacker Chemicals (USA), Inc.

It can be desirable to use a mixture of cyclodextrins. Such mixtures can complex with a wider range of odor molecules having a wider range of molecular sizes. Preferably at least a portion of such a mixture of cyclodextrins is alpha-cyclodextrin or its derivatives, gamma-cyclodextrin or its derivatives thereof, and/or beta-cyclodextrin or its derivatives.

Cyclodextrin molecules are known for their ability to form complexes with perfume ingredients and have typically been taught as a perfume carrier. The prior art teaches the use of drier-added fabric softener sheets containing high levels of cyclodextrin/perfume complexes wherein the fabrics treated with this solid cyclodextrin complex release perfume when the fabrics are rewetted. The art also teaches that cyclodextrin/perfume complexes used in aqueous rinse-added fabric softener compositions must be protected, e.g., with a hydrophobic wax coating so the cyclodextrin/perfume complexes will not decompose due to the presence of water. See U.S. Pat. No. 5,102,564 Gardlik et al., issued Apr. 7, 1992; U.S. Pat. No. 5,234,610, Gardlik et al., issued Aug. 10, 1993; U.S. Pat. No. 5,234.611 Trinh, et al., issued Aug. 10, 1993, all of said patents incorporated herein by reference. Animal litter treated with aqueous compositions of the present invention, which contain low levels of unprotected cyclodextrin/perfume complex, also exhibit perfume release upon rewetting. This phenomenon provides a benefit in that litter treated according to the present invention which contains a small amount of cyclodextrin/perfume complex as discussed hereinafter, will thus remain fresh longer, via a perfume release, when said litter is wetted. Mixtures of uncomplexed cyclodextrin and small amounts of perfume/cyclodextrin complex in the amounts disclosed hereinafter are preferred. As discussed hereinbefore, and hereinafter, the particle size of the uncomplexed cyclodextrin and the perfume/cyclodextrin complex should be small.

For reducing malodor impression on the litter herein, the cyclodextrin is preferably applied as a spray. It is preferable that the level of cyclodextrin is from about 0.001% to about 5%, preferably from about 0.01% to about 1%, more preferably from about 0.05% to about 0.6%, most preferably from about 0.1% to about 0.4%, by weight of the litter material. Litter with higher concentrations is more effective, but is not normally economical.

Compositions which can be used to retreat the litter in use can contain from about 0.03% to about 5%, preferably from about 0.5% to about 2%, cyclodextrin.

Activated Carbon Odor-Absorbing Agent

The carbon material employed herein is the material well known in commercial practice as an adsorbent for organic molecules and/or for air purification purposes. Carbon suitable for use herein is available from a variety of commercial sources under trade names such as CALGON Type "CPG", Type "PCB", Type "SGL", Type "CAL", and Type "OL." Often, such carbon material is referred to simply as "activated" carbon or "activated" charcoal. Typically, it is available in the form of extremely fine, dusty particles (e.g., 0.1–300 microns) having large surface areas (about 200 to several thousand $m^2/g$). It is to be understood that any of the "air purifying" or "activated" carbons of commerce can be used in the practice of this invention.

If the zeolites herein are optionally used in conjunction with the activated carbon, it is preferred (for aesthetics reasons) to coat the carbon with the zeolite using a binder.

Other Odor-Absorbing Agents

Other odor-absorbing agents include kieselguhr, chelating agents, chitin, pH buffered materials, and the like.

(D) PERFUME

Perfume is an important part of the animal care system. The use of desirable, refreshing perfume ingredients to formulate a "refreshing perfume", in preferred delivery systems, can make the undesirable odors more palatable to the owners. Also, use of appropriate perfume ingredients can influence the animals' behavior. For example, the right perfume ingredients in an "attractant perfume" can attract a cat to its litter box, its toys, scratching post, etc., and the right perfume in a "deterrent perfume" can influence the cat to stay away from objects such as furniture that it likes to use as a scratching post.

The refreshing perfume compositions typically, and preferably, contain ingredients with odor characteristics which are preferred by humans in order to provide a fresh impression and deodorizing benefit. Preferably, the perfume ingredients are selected predominantly from two groups of ingredients, namely, (a) volatile ingredients having a boiling point (BP) at normal pressure of less than about 260° C., and more preferably less than about 250° C., and (b) ingredients having significantly low detection threshold.

Nonlimiting examples of preferred volatile perfume ingredients are allo-ocimene, allyl caproate, allyl heptoate, amyl acetate, amyl propionate, anisic aldehyde, anisole, benzyl acetate, benzyl acetone, benzyl alcohol, benzyl butyrate, benzyl formate, benzyl iso valerate, benzyl propionate, beta gamma hexenol, camphene, carvacrol, laevo-carveol, d-carvone, laevo-carvone, cinnamyl formate, cis-3-hexenyl higlate. cis-jasmone, cis-3-hexenyl acetate, citronellol, citronellyl acetate, citronellyl isobutyrate, citronellyl nitrile, citronellyl propionate, cyclohexyl ethyl acetate, cuminic alcohol, cuminic aldehyde, Cyclal C, decyl aldehyde, dihydro myrcenol, dihydromyrcenyl acetate, dimethyl benzyl carbinol, dimethyl benzyl carbinyl acetate, dimethyl octanol, ethyl acetate, ethyl aceto acetate, ethyl amyl ketone, ethyl butyrate, ethyl hexyl ketone, ethyl phenyl acetate, eucalyptol, fenchyl acetate, fenchyl alcohol, Flor acetate (tricyclo decenyl acetate), frutene (tricyclo decenyl propionate), gamma methyl ionone, gamma-nonalactone, geraniol, geranyl acetate, geranyl formate, geranyl isobutyrate, geranyl nitrile, hexenol, hexenyl acetate, hexenyl isobutyrate, hexyl acetate, hexyl formate, hexyl neopentanoate, hexyl tiglate, hydratropic alcohol, hydroxycitronellal, alpha-ionone, beta-ionone, gamma-ionone, alpha-irone, isoamyl alcohol, isobomyl acetate, isobutyl benzoate, isononyl acetate, isononyl alcohol, isomenthol, isomenthone, para-isopropyl phenylacetaldehyde, isopulegol, isopulegyl acetate, isoquinoline, lauric aldehyde (dodecanal), Ligustral, linalool oxide, linalyl acetate, linalyl formate, menthyl acetate, methyl acetophenone, methyl amyl ketone, methyl anthranilate, methyl benzoate, methyl benzyl acetate, methyl chavicol, methyl eugenol, methyl heptenone, methyl heptine carbonate, methyl heptyl ketone, methyl hexyl ketone, methyl phenyl carbinyl acetate, alpha-iso "gamma" methyl ionone, methyl octyl acetaldehyde, nerol, neryl acetate, nonyl acetate, nonyl aldehyde, octalactone, octyl alcohol (octanol-2), octyl aldehyde, para-cymene, para-methyl acetophenone, phenyl acetaldehyde, phenyl ethyl acetate, phenyl ethyl alcohol, phenyl ethyl dimethyl carbinol, phenoxy ethanol, prenyl acetate, propyl butyrate, pulegone, rose oxide, safrole, 4-terpinenol, alpha-terpineol, terpinolene, terpinyl acetate, tetrahydro linalool, tetrahydro myrcenol, tonalid, undecenal, Veratrol, Verdox, vertenex, and Viridine.

Examples of other volatile perfume ingredients which can be used in perfume compositions of this invention are diphenyl methane, gamma-n-methyl ionone, isobutyl quinoline, eugenol, indole, beta-caryophyllene, methyl-n-methyl anthranilate, dodecalactone, lilial (p-t-bucinal), phenyl heptanol, phenyl hexanol, ethyl methyl phenyl glycidate, para-methoxy acetophenone, amyl benzoate, phenoxy ethyl proprionat, heliotropine.

The odor detection threshold of an odorous material is the lowest vapor concentration of that material which can be olfactorily detected. The odor detection threshold and some odor detection threshold values are discussed in, e.g., "Standardized Human Olfactory Thresholds", M. Devos et al, IRL Press at Oxford University Press, 1990, and "Compilation of Odor and Taste Threshold Values Data", F. A. Fazzalari, editor, ASTM Data Series DS 48A, American Society for Testing and Materials, 1978, both of said publications being incorporated by reference. The use of small amounts of perfume ingredients that have low odor detection threshold values can improve perfume odor character, even though they are not as volatile as perfume ingredients of group (a) which are given hereinabove. Perfume ingredients having significantly low detection threshold, useful in the animal litter of the present invention, are selected from the group consisting of coumarin, vanillin, ethyl vanillin, methyl dihydro isojasmonate, isoeugenol, lyral, gamma-undecalactone, gamma-dodecalactone, methyl beta naphthyl ketone, and mixtures thereof. These materials are preferably present at low levels in addition to the volatile ingredients of group (a), typically less than about 20%, preferably less than about 15%, more preferably less than about 10%, by weight of the total perfume compositions of the present invention.

Typically. at least about 50%, preferably at least about 60%, more preferably at least about 70%. and most preferably at least about 80% by weight of the perfume is composed of perfume ingredients of the above groups (a) and (b).

An optional but preferred perfume ingredient useful in the formulation of attractant perfume compositions of the present invention is nepetalactone (and its derivatives), the active ingredient of catnip. The catnip extract can also be used in place of nepetalactone. Nepetalactone (or catnip extract) should not be used in the litter since cats do not like to replace the desirable odor with the odor of their excretions. However, compositions to be applied to cat quarters and/or toys (such as scratch posts) to provide freshening and/or attracting benefits, can contain a level of nepetalactone, preferably in combination with other perfume ingredients, typically of from about 0.005% to about 5%, preferably from about 0.01% to about 3%, more preferably from about 0.05% to about 1%, by weight of the composition.

Attractant perfume compositions such as these, and especially the more dilute compositions described hereinafter, can be used both initially, and on an ongoing basis, to maintain the attractiveness of certain objects and areas to the animal, especially cats.

Repellent perfume compositions should contain, and refreshing and attractant perfume compositions should minimize, the levels of some perfume ingredients which are repulsive to animals, especially cats, that are allowed freedom of movement. These include methyl salicylate, ethyl salicylate, propyl salicylate, n-butyl salicylate, isobutyl salicylate, iso-amyl salicylate, salicylic aldehyde, cinnamic alcohol, cinnamic aldehyde, menthol, linalool, thymol, cresol, cineol, camphor, citral, terpinene, pinene, limonene, beta-myrcene, muscone, menthone, lemongrass oil, citronella oil, methyl nonyl ketone, methyl phenyl ketone, methyl amyl ketone, methyl nonyl acetaldehyde, leaf aldehyde, pelargonolactone, hinokitiol, kerosene, pyroligneous acid, dodecylbenzene, diphenyl, ethyldiphenyl, diethyldiphenyl, methylnaphthalene, nonylphenyl, dinonylphenol, dodecylphenol, phenylphenol, diphenyl ether, dibenzyl ether, methyl naphthyl ether, bis(2-chloroisopropyl) ether, gamma-alkyl-gamma-butyrolactone (e.g., gamma-n-amyl-gamma-butyrolactone), anethole, benzaldehyde, ethyl benzoate, 2-butoxyethanol, nicotine, undecan-2-one, and 3-phenylpropenal. Some of these cat repelling ingredients connote a fresh impression to human. As stated above, these ingredients should be maximized in the perfumes that are applied to objects like furniture, which the animal should avoid and minimized in the refreshing and attractant perfumes. If present, to provide the freshening effect, these repellent ingredients should be less than about 0.05%, preferably less than about 0.03%, and more preferably less than about 0.01%, by weight of the animal litter material.

In the perfume compositions to be incorporated in the animal litter herein, as discussed below, the repellent ingredients should be less than about 25%, preferably less than about 20%, and more preferably less than about 15% by weight, of the headspace vapor composition of said perfume compositions.

On the other hand, perfume compositions to be used as animal repellents should typically contain at least about 30%, preferably at least about 40%, more preferably at least about 50%, and most preferably at least 60%, by weight, of these repellent perfume ingredients.

Perfume in animal litter

The refreshing perfume compositions are typically selected for use in the animal litter of the present invention. The optional, but highly preferred, refreshing perfume is preferably present in the animal litter at an effective level to provide a freshening benefit, typically from about 0.001% to about 0.3%, preferably from about 0.005% to about 0.2%, more preferably from about 0.01% to about 0.1%, by weight of the animal litter material. Nepetalactone (or catnip extract) and perfume ingredients that repel cats should not be used in the perfume for the litter.

Some of the repellent perfume ingredients described above, which provide the freshening effect, can be present in the perfume in the animal litter. However, these repellent ingredients should be less than about 0.05%, preferably less than about 0.03%, and more preferably less than about 0.01%, by weight of the animal litter material and are preferably essentially absent. In the perfume compositions to be incorporated in the animal litter herein, the repellent ingredients should be less than about 25%, preferably less than about 20%, and more preferably less than about 15% by weight, of the headspace vapor composition of said perfume compositions. Current perfumes used in litter are believed to be higher in the repellent ingredients.

Although some "free" perfume can be present in the animal litter of the present invention, it is preferably that at least a major part of the perfume be contained or encapsulated in a carrier to prevent premature loss to the atmosphere, as well as to avoid a strong fragrance odor which can be uncomfortable to the animals. This is especially important for the desirable perfume ingredients of groups (a) and (b) above. The encapsulation can be in the form of molecular encapsulation, such as the inclusion complex with cyclodextrin, coacevate microencapsulation wherein the perfume droplet is enclosed in a solid wall material, "cellular matrix" encapsulation wherein solid particles containing perfume droplets stably held in the cells. Perfume can also be more crudely embedded in a matrix, such as a starch or sugar matrix.

The encapsulated perfume can be released either by a moisture activation and/or a pressure activation mechanism. Moisture-activated microcapsules release perfume upon being wetted, e.g., by the animal urine. Pressure-activated microcapsules release perfume when the shell wall is broken by, e.g., the scratching or stepping of the animals on the litter. Some microcapsules can be activated both by moisture and pressure.

The selection for the most suitable method of perfume delivery takes into account the effectiveness, the efficiency, and the cost of each method. Cyclodextrin/perfume complex is preferred for its effectiveness and ease of processing. The complex protects and retains the perfume ingredients very well from physical effects (e.g., no rupture/perfume loss during processing, packaging, shipping, and storing of the animal litter, or perfume loss from diffusion) and from chemical effects (e.g., degradation during storage). However, the perfume loading in the cyclodextrin complex is fairly low, e.g., from about 10% to about 18% in beta-cyclodextrin/perfume complex.

Perfume microcapsules, e.g., coacevate microcapsule where the perfume droplet is enclosed in a solid wall material or "cellular" microcapsule where a solid particle contains perfume droplets stably held in the cells, are preferred for their perfume loading which can be as high as 60–80%. The perfume release upon activation, e.g., in presence of moisture and/or pressure, is effective. However, the encapsulation process is more demanding, and perfume leakage due to breakage of the microcapsules during processing, packaging, shipping, and storing of the animal litter does tend to occur. There is a need to balance the rigidity of the microcapsule to avoid undesirable and untimely breakage and the desirable frangibility to release perfume by pressure, e.g., from the stepping or scratching by the animals. Moisture activation is normally a more desirable and effective method of perfume release than pressure activation. However, mixtures of particles that can be activated by both modes can be especially desirable, since sometimes, the amount of moisture associated with elimination products is quite low.

Porous particles can also be used to retain perfume and release it slowly in use. The crude matrix particles where the perfume is embedded in a matrix, such as a starch or sugar matrix are inexpensive and easy to produce. The perfume loading is medium. However, the activation to release perfume is normally less effective than the encapsulation methods described herein above. A nonlimiting example of such porous particles is starch granules, as are disclosed by Whistler et al in Food Technology, July 1994, pp. 104–105, incorporated wherein by reference. The perfume is filled into the starch granules and is retained, apparently, by capillarity forces. The perfume loading can be as high as about 30% to about 50%. The perfume is released slowly and continuously by diffusion. The filled particles can be coated with suitable materials to improve perfume retention. The preferred particle size is from about 10 microns to about 100 mucrons, more preferably from about 15 microns to about 60 microns. The perfume-filled porous particles are used when a continuous perfume release is desired. But they are not preferred if one wants to have the perfume released only when the animals start using the litter.

The animal litter of the present invention can also contain pro-perfumes. A pro-perfume is a normally nonvolatile molecule which consists of a volatile perfume ingredient covalently bonded to another moiety by a labile covalent bond. In use, the pro-perfume is decomposed to release the volatile perfume ingredient. The pro-perfumes useful in the present invention is selected from the group consisting of complexes of bisulfite with perfume ingredients having an aldehyde or ketone functional groups, and esters of phosphoric acids, and sulfuric acids with perfume ingredients having a hydroxyl group. The bisulfite complex can be prepared according to the disclosure in U.S. Pat. No. 5,267,531, issued to Appel et al., issued Dec. 7, 1993, said patent being incorporated herein by reference. It is believed that the pro-perfumes work in the following manner. The nonvolatile pro-perfumes are sprayed on the animal litter. A small amount of urea in the urine is decomposed to form some ammonia, even in the presence of a urease inhibitor. As the pH rises due to the presence of ammonia, the pro-perfumes are hydrolyzed to release the volatile perfume ingredients, to mask the ammonia odor. Since most pro-perfumes are not very volatile, they can be applied to the litter material without the need for encapsulation. However, if a pro-perfume is chemically labile, it is also advantageous to protect it via encapsulation, and only release it in use.

Cyclodextrin/Perfume Inclusion Complexes

The perfume/cyclodextrin inclusion complexes useful herein are formed in any of the ways known in the art. Typically, the complexes are formed either by bringing the perfune and the cyclodextrin together in a suitable solvent, e.g., water, or, preferably, by kneading/slurrying the ingredients together in the presence of a suitable, preferably minimal, amount of solvent, preferably water. The kneading/slurrying method is particularly desirable because it produces smaller complex particles and requires the use of less solvent, eliminating or reducing the need to further reduce particle size and separate excess solvent. Disclosures of complex formation can be found in Atwood, J. L., J. E. D. Davies & D. D. MacNichol, (Ed.): *Inclusion Compounds*, Vol. III, Academic Press (1984), especially Chapter 11, Atwood, J. L. and J. E. D. Davies (Ed.): *Proceedings of the Second International Symposium of Cyclodextrins* Tokyo, Japan, (July, 1984), and J. Szejtli, *Cyclodextrin Technology*, Kluwer Academic Publishers (1988), said publications incorporated herein by reference.

In general, perfume/cyclodextrin complexes have a molar ratio of perfume compound to cyclodextrin of about 1:1. However, the molar ratio can be either higher or lower, depending on the size of the perfume compound and the identity of the cyclodextrin compound. The molar ratio can be determined by forming a saturated solution of the cyclodextrin and adding the perfume to form the complex. In general the complex will precipitate readily. If not, the complex can usually be precipitated by the addition of electrolyte, change of pH, cooling, etc. The complex can then be analyzed to determine the ratio of perfume to cyclodextrin.

The actual complexes are determined by the size of the cavity in the cyclodextrin and the size of the perfume molecule. Desirable complexes can be formed using mixtures of cyclodextrins since perfumes are normally mixtures of materials that vary widely in size. It is usually desirable that at least a majority of the material be alpha-, beta-, and/or gamma-cyclodextrin, more preferably beta-cyclodextrin. The content of the perfume in the beta-cyclodextrin complex is typically from about 5% to about 15%, more normally from about 7% to about 12%.

Continuous complexation operation usually involves the use of supersaturated solutions, kneading/slurrying method, and/or temperature manipulation, e.g., heating and then either cooling, freeze-drying, etc. The complexes are dried to a dry powder to make the desired composition. In general, the fewest possible process steps are preferred to avoid loss of perfume.

Complexes of this invention having a particle size of less than about 12 microns, preferably less than about 10 microns, more preferably less than about 8 microns, and even more preferably less than about 5 microns, improve the release, especially the speed of release of the perfume when the complexes are wetted. The particle size is typically between about 0.001 and 10 microns, preferably between about 0.05 and 5 microns. It is highly desirable that at least an effective amount of the perfume be in complexes having the said particle sizes. It is desirable that at least about 75%, preferably at least about 80%, more preferably at least about 90%, and even more preferably at least about 100%, of the complex that is present have the said particle sizes.

These small particles of the invention are conveniently prepared by kneading methods and/or grinding techniques. Cyclodextrin complexes with large particle sizes can be pulverized to obtain the desired smaller particles of less than about 12 microns by using, e.g., a fluid energy mill. Examples of fluid energy mills are given hereinbefore.

Some caution should be observed in that some of the dry complex particles may remain agglomerated, and the aggregates can be easily broken by mechanical action.

At least an effective amount of the cyclodextrin/perfume complex is to be applied to the litter material of this invention in order to deliver the desired levels of perfume. Effective amounts are typically in the range of from about 0.01% to about 3%, preferably from about 0.04% to about 2%, more preferably from about 0.07% to about 1%, by weight of the animal litter material.

Pressure-Activated Perfume Microcapsules

Microcapsules suitable for affixation to the inventive animal litter, as disclosed in U.S. Pat. No. 4,407,231, Colbom et al, issued Oct. 4, 1983, incorporated herein by reference, can have a diameter of from about 25 microns to about 200 microns, and more preferably have a diameter of from about 50 microns to about 110 microns. The microcapsules include a fragrance or a deodorizer encapsulated therein, and the fragrance or deodorizer preferably is about 75 weight % to about 85 weight % of the microcapsules.

The microcapsules are adapted to release the fragrance in response to contact between exterior surfaces of the particles during relative movement of the particles, such as occurs during agitation by the animal. This release of fragrance or deodorizer occurs when the microcapsules rupture. Suitable microcapsules rupture when subjected to a force of from about 200 psi (1400 kPa) to about 1600 psi (11000 kPa), more preferably from about 300 psi (2300 kPa) to about 800 psi (5600 kPa).

Microcapsules suitable for affixation to absorbent particles in accordance with the present invention are preferably formed of a substantially water insoluble wall material, such as a urea formaldehyde polymer. Suitable microcapsules for the present invention can be made, for example, in accordance with the teaching of U.S. Pat. No. 3,516,941, inventor Matson, issued Jun. 23, 1970 (incorporated herein by reference).

The affixed microcapsules are desirably sufficiently frangible so that they release the perfume after more harsh contact between exterior surfaces during relative movement of the particles, e.g., by the "scratching" of the animal, but should be sufficiently strong to resist breakage during packaging, shipping and storing of the animal litter. Although some breakage, or rupture, of the affixed microcapsules does tend to occur during packaging, shipping, and storing, sufficient microcapsules should survive to provide selective fragrance release. Sufficient amount of perfume microcapsules should be used to deliver the desired levels of perfume, depending on the perfume loading of the microcapsules. Effective amounts of microcapsules are typically in the range of from about 0.002% to about 0.6%, preferably from about 0.007% to about 0.4%, more preferably from about 0.01% to about 0.2%, by weight of the animal litter material.

Moisture-Activated Cellular Perfume Microcapsules

Water-soluble cellular matrix perfume microcapsules are solid particles containing perfume stably held in the cells. The water-soluble matrix material comprises mainly polysaccharide and polyhydroxy compounds. The polysaccharides are preferably higher polysaccharides of the non-sweet, colloidally-soluble types, such as natural gums, e.g., gum arabic, starch derivatives, dextrinized and hydrolyzed starches, and the like. The polyhydroxy compounds are preferably alcohols, plant-type sugars, lactones, monoethers, and acetals. The cellular matrix microcapsules useful in the present invention are prepared by, e.g., (1) forming an aqueous phase of the polysaccharide and polyhydroxy compound in proper proportions, with added emulsifier if necessary or desirable; (2) emulsifying the perfumes in the aqueous phase; and (3) removing moisture while the mass is plastic or flowable, e.g., by spray drying droplets of the emulsion. The matrix materials and process details are disclosed in, e.g., U.S. Pat. No. 3,971,852, Brenner et al., issued Jul. 27, 1976, which is incorporated herein by reference.

Moisture-activated perfume microcapsules of the cellular type can be obtained commercially, e.g., as IN-CAP® from Polak's Frutal Works, Inc., Middletown, N.Y.; and as Optilok System® encapsulated perfumes from Encapsulated Technology, Inc., Nyack, N.Y.

Water-soluble cellular matrix perfume microcapsules preferably have size of from about 0.5 micron to about 300 microns, more preferably from about 1 micron to about 200 microns, most preferably from about 2 microns to about 100 microns. Sufficient amount of moisture-activated perfume microcapsules should be used to deliver the desired levels of perfume, depending on the perfume loading of the microcapsules. Effective amounts of miciocapsules are typically in the range of from about 0.002% to about 0.6%, preferably from about 0.007% to about 0.4%, more preferably from about 0.01% to about 0.2%, by weight of the animal litter material.

Cruder starch matrix perfume particles can be prepared according to the disclosure in U.S. Pat. No. 5,267,531, Appel et al., issued Dec. 7, 1993, said patent being incorporated herein by reference. The perfume oil is emulsified with various starches and water for a period of two hours. The emulsion is then spray dried and checked for proper oil content.

Perfume in compositions used for replenishment

The combination of refreshing, attractant, and repellent perfumes, properly applied and continually refreshed, contributes to maintaining control over the animal's behavior and can aid in the training of the animal. Accordingly, the animal care system comprises a method in which an animal attractant perfume, an animal deterrent perfume. and/or a refreshing perfume, are applied at effective levels to provide the desired effects (deterrence, avoidance, and refreshment) to various areas and/or objects which the animal owner selects with respect to an animal that has a relatively high degree of freedom of movement. For example, the animal attractant perfume can desirably be applied to toys, scratching posts, etc. for cats and the animal repellent perfume can be applied to furniture, drapes, etc. Repellent perfume compositions are desirable additives to compositions used to clean up unwanted excretions, so as to lower the likelihood of a reoccurrence. For animals without much freedom of movement, like gerbils, mice, rats, guinea pigs, rabbits, etc. the perfume of choice will normally be either a refreshing perfume, or an attractant perfume to make the animal happier.

The above perfume compositions can be used to treat litter, animal toys, etc. as they are originally manufactured. In the original treatment, it is preferred that the perfume be protected. These same perfume compositions can also be used as is, or in diluted form compositions, to treat animal litter, toys, etc. to replenish the perfume and prolong the desired effect. Typically these compositions are dilute with respect to the perfume.

The perfume materials disclosed above for the refreshing perfumes are preferred for most uses. However, attractant and repellent materials can also be incorporated. As disclosed hereinbefore, the attractant materials and perfumes are best for application to toys and other items like scratching posts, whereas the repellent materials and perfumes are preferably used on items like furniture, drapes, spots on carpets, plants, etc. where the owner does not want the pet to be. The animal litter can be refreshed by application of a dilute composition comprising refreshing perfume.

Preferably the freshening composition contains an effective amount of perfume to provide the freshening fragrance when first sprayed and some lingering fragrance with time. Effective level of perfume is from about 0.01% to about 1%, more preferably from about 0.01% to about 0.5%, most preferably from about 0.015% to about 0.3%, by weight of the composition.

(E) AQUEOUS CARRIER

Aqueous solutions are preferred in the present invention for the preparation of the animal litter and/or freshening the animal litter. The preferred aqueous carrier of the present invention is water. The water which is used can be distilled, deionized. or tap water. Water containing a small amount of low molecular weight monohydric alcohols, e.g., ethanol, methanol, and isopropanol, or polyols, such as ethylene glycol and propylene glycol, can also be useful. However, the volatile low molecular weight monohydric alcohols such as ethanol and/or isopropanol should be limited since these volatile organic compounds can contribute both to flammability problems and environmental pollution problem. If small amounts of low molecular weight monohydric alcohols are present in the composition of the present invention due to the addition of these alcohols to such things as perfumes and as stabilizers for some preservatives, it is preferably that the level of monohydric alcohol be less than about 10%, preferably less than about 5%, more preferably less than about 3%, by weight of the composition used to prepare the animal litter.

Aqueous solutions can also be used to treat the litter during use, to "refreshen" the litter. These aqueous solutions can also be used to treat "accidents" where the animal soils rugs, carpets, furniture, clothes, etc.

(F) SOLUBILIZING AID

The aqueous composition used to form the animal litter of the present invention can optionally, but preferably, contain a solubilizing aid to solubilize any excess hydrophobic organic materials, especially the perfume, and also optional ingredients which can be added to the composition, e.g., insect repelling agent, antioxidant, etc., that are not readily soluble in the composition. A suitable solubilizing aid is surfactant or wetting agent. In a spray product, it is preferably that the surfactant is a non-foaming or low-foaming surfactant. Suitable surfactants are nonionic surfactants, cationic surfactants, amphoteric surfactants, zwitterionic surfactants, and mixtures thereof, preferably nonionic surfactants and cationic surfactants, and mixtures thereof. Anionic surfactants are not preferred when the preferred urease inhibiting transition metal ions are present, because they can form water-insoluble salts with the metal ions. Suitable surfactants can be emulsifiers and/or detersive surfactants. Mixtures of emulsifiers and detersive surfactants are also preferred. When a surfactant containing one, or more, alkyl group is used, it is preferred that it contain relatively short alkyl chains of from about 5 to about 14 carbon atoms. Typical nonionic surfactants are polyethylene glycol-polypropylene glycol block copolymers, such as Pluronic® and Pluronic R® surfactants from BASF; Tetronic® and Tetronic R® surfactants from BASF, ethoxylated branched aliphatic diols, such as Surfynol® surfactants from Air Products; ethoxylated alkyl phenols, such as Igepal® surfactants from Rhône-Poulenc; ethoxylated aliphatic alcohols and carboxylic acids; polyethylene glycol diesters of fatty acids; and mixtures thereof. Preferably, said solubilizing aid is a nonionic surfactant selected from the group consisting of fatty acid esters of ethoxylated sorbitans. More preferably said solubilizing aid is selected from the group consisting of mixtures of laurate esters of sorbitol and sorbitol anhydrides; mixtures of stearate esters of sorbitol and sorbitol anhydrides; and mixtures of oleate esters of sorbitol and sorbitol anhydrides. Even more preferably said solubilizing aid is selected from the group consisting of Polysorbate 20, which is a mixture of laurate esters of sorbitol and sorbitol anhydrides consisting predominantly of the monoester, condensed with about 20 moles of ethylene oxide; Polysorbate 60 which is a mixture of stearate esters of sorbitol and sorbitol anhydride, consisting predominantly of the monoester, condensed with about 20 moles of ethylene oxide; Polysorbate 80 which is a mixture of oleate esters of sorbitol and sorbitol anhydrides, consisting predominantly of the monoester, condensed with about 20 moles of ethylene oxide; and mixtures thereof. Most preferably, said solubilizing aid is Polysorbate 60. Preferred cationic surfactants are di($C_8$–$C_{12}$ alkyl)di($C_1$–$C_2$ alkyl)ammonium halides, alkylbenzyldimethylammonium halides, amine oxides, and mixtures thereof. Preferred amphoteric surfactants are the betaines. It is preferred that the surfactant have good wetting properties. Also preferred are surfactants that have the hydrophilic groups between hydrophobic chains, such as, Pluronic R surfactants, Surfynol surfactants, polyethylene glycol diesters of fatty acids, fatty acid esters of ethoxylated sorbitans, di($C_8$–$C_{12}$ alkyl)di($C_1$–$C_2$ alkyl) ammonium halides. and mixtures thereof; surfactants that have hydrophilic groups situated at the extremities of the hydrophobic chain, such as Pluronic surfactants; and mixtures thereof. Mixtures of these surfactants and other types of surfactants are also preferred to form no-foaming or low-foaming solubilizing agents. Polyalkylene glycol can be used as defoaming agent in combination with the solubilizing agents.

When a solubilizing aid is used in the composition of the present invention, more specifically when fatty acid esters of ethoxylated sorbitans are used as the solubilizing aid, it is preferable to use the process of high shear milling in order aid in the incorporation of excess hydrophobic organic material.

The solubilizing aids disclosed in the present invention, specifically the fatty acid esters of ethoxylated sorbitan, can be used in any type of composition where excess hydrophobic organic material, particularly perfume, separates out of solution and needs assistance to be incorporated into the composition.

When the solubilizing agent is present, it is typically present at a level of from about 0.02% to about 3%, by weight of the composition, more preferably from about 0.05% to about 1%, by weight of the composition, most preferably from about 0.1% to about 0.3%, by weight of the composition.

(G) BINDING AID

A preferred method of affixing solid powder active ingredients, such as uncomplexed cyclodextrin powder, perfume/cyclodextrin complex, and perfume microcapsules, is to form a slurry of said ingredients in a liquid carrier, preferably water, and then the slurry is sprayed onto the animal litter substrate. The slurry can also be separately packaged in a suitable spray dispenser for spraying onto litter particles by an animal's owner.

The slurry can optionally include a suitable binding agent in an effective amount to help affix (improve the affixation) the solid powder active ingredients to the animal litter substrate when the slurry is sprayed thereon. More particularly, suitable binding agents will function to form a bond between the solid powder or microcapsules and exterior surfaces of the substrates which is strong enough to affix and hold at least a major portion of the solid powder active ingredients onto the substrate during handling, such as shaking, pouring and the like, as is encountered in packaging procedures.

Sufficient of the binding agent is preferably an amount of at least about 3%, preferably from about 5% to about 20%, by weight of the solid powder active ingredients in the slurry. Preferred binding agents include polyethylene glycol with an average molecular weight of at least about 2,000, more preferably at least about 3,000, acrylic emulsions (such as are commercially available from Rohm & Haas as Rhoplex AC 61) and neoprene latex. A preferred adhesive agent is neoprene latex 735A, commercially available from DuPont.

The binding agent is desirably selected from materials which are compatible with the suspended actives and other ingredients. Thus materials which can substantially form complex with cyclodextrin should not be used to suspend uncomplexed cyclodextrin and/or cyclodextrin/perfume complex powder, and polyacrylates should not be used in the presence of water soluble, heavy transition metal ions, such as zinc ions. Polyethylene glycols are particularly suitable to be used with cyclodextrin and cyclodextrin complexes. Also the binding agent should be dispersible in the liquid carrier, with water being the most preferred liquid carrier.

(H) SUSPENSION AID

A suspension aid is optionally used to suspend solid powder active ingredients, such as uncomplexed cyclodextrin powder, perfume/cyclodextrin complex, and perfume microcapsules, so that they are fairly evenly dispersed to form a relatively evenly distributed layer upon the substrate's surface when the slurry is sprayed thereon. More particularly, for commercial preparation of the animal litter of this invention, the suspension agent should be present in a sufficient amount to provide suspension stability for the slurry (e.g., prevent separation, or settling, of the microcapsules in the slurry), so that the slurry can be pumped and sprayed in metered amounts over a period of time. That is, the suspension agent preferably provides a stably suspended slurry for a length of time, e.g., at least about 12 hours, more preferably for greater than about 24 hours. The suspension agent should be dispersible in the slurry composition, and preferably thickens the slurry to a viscosity of at least about 100 centipoise.

Preferred materials for use as the suspension agent are polyacrylic acids, such as are available from B. F. Goodrich as Carbopol (e.g., neutralized Carbopol 941) and from Rohm & Haas as Acrysol, which are very effective (in the neutralized form) in stably suspending microcapsules of the slurry at levels as low as about 0.01% to about 1%, more preferably from about 0.05% to about 0.2%, by weight of the slurry.

Other preferred materials are particulate clays, such as smectite clay. A preferred clay suspending agent is calcium bentonite clay, available from Southern Clay Products under the trade name Bentolite® L. The clay suspension agent is preferably present at a level of from about 0.1% to about 10%, more preferably from about 0.3% to about 5%, by weight of the slurry.

The suspension agent must desirably be selected from materials which are compatible with the suspended actives and other ingredients. Thus materials which can substantially form complex with cyclodextrin should not be used to suspend uncomplexed cyclodextrin and/or cyclodextrin/perfume complex powder, and polyacrylates and ion-exchangeable clays should not be used in the presence of water soluble, heavy transition metal ions, such as zinc ions. Also the suspension agent should be dispersible in the liquid carrier, with water being the most preferred liquid carrier.

(I) Cleaning Ingredients, Including Enzymes

Enzymes are desirable components for the purpose of cleaning and for destroying animal excretions, including regurgitated. Enzymes other than ureases can be used to destroy the soils, especially in aqueous solutions used to treat the litter in use and accidental soils. Proteases are especially desirable. Proteases can actually be urease inhibitors. The activity of commercial enzymes depends very much on the type and purity of the enzyme being considered. Enzymes that are water soluble proteases like pepsin, tripsin, ficin, bromelin, papain, rennin, and mixtures thereof are particularly useful. In the claims herein, when a material can be defined as having more than one function, it is defined as the first type of material listed.

Enzymes are normally incorporated at levels sufficient to provide up to about 5 mg by weight, more typically from about 0.001 mg to about 3 mg, preferably from about 0.002 mg to about 1 mg of active enzyme per gram of the aqueous compositions. Stated otherwise, the aqueous compositions herein can comprise from about 0.0001% to about 0.5%, preferably 0.005%–0.3% by weight of a commercial enzyme preparation. Protease enzymes are usually present in such commercial preparations at levels sufficient to provide from 0.0005 to 0.1 Anson units (AU) of activity per gram of aqueous composition.

Nonlimiting examples of suitable, commercially available, water soluble proteases are pepsin, tripsin, ficin, bromelin, papain, rennin, and mixtures thereof. Papain can be isolated, e.g., from papaya latex, and is available commercially in the purified form of up to, e.g., about 80% protein, or cruder, technical grade of much lower activity. Other suitable examples of proteases are the subtilisins which are obtained from particular strains of *B. subtilis* and *B. licheniforms*. Another suitable protease is obtained from a strain of Bacillus, having maximum activity throughout the pH range of 8–12, developed and sold by Novo Industries A/S under the registered trade name ESPERASE®. The preparation of this enzyme and analogous enzymes is described in British Patent Specification No. 1,243,784 of Novo. Proteolytic enzymes suitable for removing protein-based stains that are commercially available include those sold under the trade names ALCALASE® and SAVINASE® by Novo Industries A/S (Denmark) and MAXATASE® by International Bio-Synthetics, Inc. (The Netherlands). Other proteases include Protease A (see European Patent Application 130,756, published Jan. 9, 1985); Protease B (see European Patent Application Serial No. 87303761.8, filed Apr. 28, 1987, and European Patent Application 130,756, Bott et al, published Jan. 9, 1985); and proteases made by Genencor International, Inc., according to one or more of the following patents: Caldwell et al, U.S. Pat. Nos. 5,185,258, 5,204,015 and 5,244,791.

Amylases include, for example, α-amylases described in British Patent Specification No. 1,296,839 (Novo), RAPIDASE(®, International Bio-Synthetics, Inc. and TERMAMYL®, Novo Industries.

Suitable lipase enzymes for usage herein include those produced by microorganisms of the Pseudomonas group, such as *Pseudomonas stutzeri* ATCC 19.154, as disclosed in British Patent 1,372,034. See also lipases in Japanese Patent Application 53,20487, laid open to public inspection on Feb. 24, 1978. This lipase is available from Amano Pharmaceutical Co. Ltd., Nagoya, Japan, under the trade name Lipase P "Amano," hereinafter referred to as "Amano-P." Other commercial lipases include Amano-CES, lipases ex Chromobacter viscosum, e.g. *Chromobacter viscosum* var. *lipolyticum NRRLB* 3673, commercially available from Toyo Jozo Co., Tagata, Japan; and further Chromobacter viscosum lipases from U.S. Biochemical Corp., U.S.A. and Disoynth Co., The Netherlands, and lipases ex *Pseudomonas gladioli*. The LIPOLASE® enzyme derived from *Humicola lanuginosa* and commercially available from Novo (see also EPO 341,947) is a preferred lipase for use herein.

A wide range of enzyme materials and means for their incorporation into cleaning compositions are also disclosed in U.S. Pat. No. 3,553,139, issued Jan. 5, 1971 to McCarty et al. Enzymes are further disclosed in U.S. Pat. No. 4,101,457, Place et al, issued Jul. 18, 1978, and in U.S. Pat. No. 4,507,219, Hughes, issued Mar. 26, 1985. Enzyme materials useful for liquid detergent formulations, and their incorporation into such formulations, are disclosed in U.S. Pat. No. 4,261,868, Hora et al, issued Apr. 14, 1981. Enzymes for use in detergents can be stabilized by various techniques, e.g., those disclosed and exemplified in U.S. Pat. No. 3,600,319, issued Aug. 17, 1971 to Gedge, et al., European Patent Application Publication No. 0 199 405, Application No. 86200586.5, published Oct. 29, 1986, Venegas, and in U.S. Pat. No. 3,519,570. All of the above patents and applications are incorporated herein, at least in pertinent part.

Enzyme-polyethylene glycol conjugates are also preferred. Such polyethylene glycol (PEG) derivatives of enzymes, wherein the PEG or alkoxy-PEG moieties are coupled to the protein molecule through, e.g., secondary amine linkages. Suitable derivatization decreases immunogenicity, thus minimizes allergic reactions, while still maintains some enzymatic activity. An example of protease-PEG's is PEG-subtilisin Carlsberg from *B. lichenniformis* coupled to methoxy-PEGs through secondary amine linkage, and is available from Sigma-Aldrich Corp., St Louis, Mo.

Other cleaning components are the typical detergent surfactants at a level of from about 0.001% to about 1%, preferably from about 0.005% to about 0.5%, more preferably from about 0.05% to about 0.3% by weight of the composition. Detersive surfactants utilized can be of the anionic, nonionic, zwitterionic, ampholytic or cationic type or can comprise compatible mixtures of these types. Detergent surfactants useful herein are described in U.S. Pat. No. 3,664,961, Norris, issued May 23, 1972, U.S. Pat. No. 3,919,678, Laughlin et al., issued Dec. 30, 1975, U.S. Pat. No. 4,222,905, Cockrell, issued Sep. 16, 1980, and in U.S. Pat. No. 4,239,659, Murphy, issued Dec. 16, 1980. All of these patents are incorporated herein by reference.

Detergent builders can optionally be included in the compositions herein to assist in controlling mineral hardness. Inorganic as well as organic builders can be used. Builders are typically used to assist in the removal of particulate soils.

The level of builder, when present in the compositions, will typically comprise from about 0.1% to about 5%, more typically about 0.5% to about 1%, by weight, of detergent builder.

Inorganic P-containing detergent builders include, but are not limited to, the alkali metal, ammonium and alkanolammonium salts of polyphosphates (exemplified by the tripolyphosphates, pyrophosphates, and glassy polymeric meta-phosphates) and/or phosphonates. Examples of alkali metal phosphates are sodium and/or potassium tripolyphosphates, pyrophosphates and/or orthophosphates. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used.

Examples of suitable nonphosphorus, inorganic builders include the silicates, borates phytic acid, carbonates (including bicarbonates and sesquicarbonates), sulfates, and aluminosilicates. Particularly preferred are sodium and potassium carbonate, bicarbonate, sesquicarbonate, tetraborate decahydrate, and silicates having a weight ratio of $SiO_2$ to alkali metal oxide of from about 0.5 to about 4.0, preferably from about 1.0 to about 2.4. Examples of silicate builders are the alkali metal silicates, particularly those having a $SiO_2:Na_2O$ ratio in the range 1.6:1 to 3.2:1. Also, crystalline layered silicates such as those discussed in Corkill et al, U.S. Pat. No. 4,605,509, incorporated herein by reference, are suitable for use in the detergent composition of the invention. Other layered sodium silicates are described in U.S. Pat. No. 4,664,839, issued May 12, 1987 to H. P. Rieck. NaSKS-6 is the trademark for a crystalline layered silicate marketed by Hoechst (commonly abbreviated herein as "SKS-6"). Unlike zeolite builders, the Na SKS-6 silicate builder does not contain aluminum. NaSKS-6 has the delta-$Na_2SiO_5$ morphology form of layered silicate. It can be prepared by methods such as those described in German DE-A-3,417,649 and DE-A-3,742,043. SKS-6 is a highly preferred layered silicate for use herein, but other such layered silicates, such as those having the general formula $NaMSi_xO_{2x+1}\cdot yH_2O$ wherein M is sodium or hydrogen, x is a number from 1.9 to 4. preferably 2, and y is a number from 0 to 20, preferably 0 can be used herein. Various other layered silicates from Hoechst include NaSKS-5, NaSKS-7 and NaSKS-11 as the alpha, beta and garnrna forms. As noted above, the delta-$Na_2SiO_5$ (NaSKS-6 form) is most preferred for use herein. Other silicates can also be useful such as for example magnesium silicate, which can serve as a crispening agent in granular formulations, as a stabilizing agent for oxygen bleaches, and as a component of suds control systems.

Examples of carbonate builders are the alkaline earth and alkali metal carbonates as disclosed in German Patent Application No. 2,321,001 published on Nov. 15, 1973.

Water-soluble, nonphosphorus organic builders useful herein include the various alkali metal, ammonium and/or substituted ammonium polyacetates, carboxylates, polycarboxylates and polyhydroxy sulfonates. A wide variety of polycarboxylate compounds are suitable. As used herein, "polycarboxylate" refers to compounds having a plurality of carboxylate groups, preferably at least 3 carboxylates. Polycarboxylate builders can generally be added to the composition in acid form, but can also be added in the form of a neutralized salt. When utilized in salt form, alkali metals, such as sodium, potassium, and lithium, or alkanolammonium salts are preferred.

Particularly preferred polycarboxylate builders the ether carboxylate builders. The ether polycarboxylates, including oxydisuccinate, are disclosed in, e.g., Berg, U.S. Pat. No. 3,128,287, issued Apr. 7, 1964, and Lamberti et al, U.S. Pat. No. 3,635,830, issued Jan. 18, 1972. See also "TMS/TDS" builders of U.S. Pat. No. 4,663,071, issued to Bush et al, on May 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance due to their availability from renewable resources and their biodegradability. Oxydisuccinates are also useful.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986. Useful succinic acid builders include the $C_5$–$C_{20}$ alkyl and alkenyl succinic acids and salts thereof. A particularly preferred compound of this type is dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Other suitable polycarboxylates are disclosed in U.S. Pat. No. 3,308,067, Diehl, issued Mar. 7, 1967. See also Diehl U.S. Pat. No. 3,723,322. Still other suitable polycarboxylates for use herein are the polyacetal carboxylates described in U.S. Pat. No. 4,144,226, issued Mar. 13, 1979 to Crutchfield et al, and U.S. Pat. No. 4,246,495, issued Mar. 27, 1979 to Crutchfield et al, both of which are incorporated herein by reference.

Fatty acids, e.g., $C_{12}$–$C_{18}$ monocarboxylic acids, can also be incorporated into the compositions alone. or in combination with the aforesaid builders, especially citrate and/or the succinate builders, to provide additional builder activity. Such use of fatty acids will generally result in a diminution of sudsing, which should be taken into account by the formulator.

(J) OTHER OPTIONAL INGREDIENTS

Adjuvants can be optionally added to the animal litter herein for their known purposes. Such adjuvants include, but are not limited to, preservatives, insect repelling agents, colorants, antioxidants, and mixtures thereof.

(II) Behavior Control Products

The animal care system herein comprises products that control animal behavior, primarily by the presence and selection of perfumes as disclosed hereinbefore. These products are preferably aqueous, containing the aqueous carrier described hereinbefore, optionally, solubilizing aid as disclosed hereinbefore, and an effective amount of the perfume. The products are preferably packaged in containers having spray means, and preferably in association with instructions for using the product to provide the indicated control.

(A) ANIMAL REPELLENT PRODUCT

The animal, normally cat, repellent compositions contain an effective amount, of from about 0.01% to about 6%, preferably from about 0.05% to about 4%, more preferably from about 0.1% to about 2%, of the repellent perfumes. Repellent perftimes contains at least about 40%, preferably at least about 50%, more preferably at least about 60%, of repellent perfume ingredients described hereinbefore. These perfumes can deter the animal from remaining in areas that the owner establishes. The products normally contain the aqueous carrier and optional solubilizing aid and/or solvents such as ethyl alcohol. In order to provide not only animal repellency, but also a pleasing effect to humans, the repellent perfumes preferably contain at least four repellent perfume ingredients, more preferably at least five repellent ingredients, and even more preferably at least six repellent ingredients, with no single ingredient comprising more than about 40%, and no two ingredients comprising more than about 50% of the repellent perfume composition. The perfume, in addition to the repellent ingredients, can also contain a substantial amount, e.g., from about 1% to about 60%, preferably from about 5% to about 50%, more preferably from about 10% to about 40%, of ingredients that provide a freshness impression to humans, as discussed hereinbefore.

(B) ANIMAL ATTRACTANT PRODUCT

The animal attractant composition contains ingredients to attract the animal, especially nepetelactone and its derivatives such as dihydronepetalactone for cats. Typically such compositions contain an effective amount, of from about 0.001% to about 5%, preferably from about 0.005% to about 3%, more preferably from about 0.01% to about 2%, of the attractant perfumes described hereinbefore. These products can attract the animal to the areas where the owner wants the animal to spend time. For example, the toys, scratch post, cage for bedding area, transport cage, etc. can be made more desirable. It is especially desirable to have a way of encouraging cats to spend more time in desirable areas. When the attractant product is used in combination with the repellent product, there is positive reinforcement for the desired behavior.

The products normally contain the aqueous carrier and optional solubilizing aid and/or solvents such as ethyl alcohol. The perfume contains not only the attractant ingredients, but also a substantial amount of from about 0.005% to about 5%, preferably from about 0.01% to about 3%, more preferably from about 0.05% to about 2%, of ingredients that provide freshness impression to humans, as discussed hereinbefore.

(III) Freshening and Cleaning Products (A) FRESHENING PRODUCT

The freshening composition herein is similar to the compositions used to prepare the litter, but with the addition of more aqueous carrier, e.g., at a level of from about 80% to about 99%, preferably from about 85% to about 99%, more preferably from about 90% to about 98%. The freshening products do not contain either repellent perfume ingredients or attractant perfume ingredients. It is preferred that the freshening compositions contain a freshening perfume at a level of from about 0.001% to about 5%, preferably from about 0.01% to about 1%, more preferably from about 0.05% to about 0.5%, as well as a mixture of material to control the creation of odor (B) at a level of from about 0.01% to about 10%, preferably from about 0.1% to about 5%, more preferably from about 0.5% to about 2%, and the material for absorbing odor (C) disclosed hereinbefore at a level of from about 0.05% to about 10%, preferably from about 0.1% to about 5%, more preferably from about 0.5% to about 2%, by weight of the freshening composition. The composition also contains, where necessary, solubilizing aid and/or suspension aid as described hereinbefore. The preferred material (B) is water soluble heavy metal salt, more preferably water soluble zinc and/or copper salts, as described hereinbefore. The preferred material (C) is soluble cyclodextrin as described hereinbefore.

Like the litter herein, the perfume should not have either attractant or repellent perfume ingredients, except possibly in very small amounts, preferably in non-effective amounts for their primary purpose.

A freshening product is a very effective way to increase the effective life of a litter, especially one that clumps. The clumps are removed, and the surrounding area is specifically treated with the freshening product to increase the effective levels of the ingredients that have been used up by the first excretion.

(B) CLEANING PRODUCT

The cleaning composition herein is primarily for cleaning up a pet's "accidents", e.g. excretions, and contains a freshening perfume, an aqueous carrier and optional solubilizing and/or suspending aids. The levels of perfume and liquid carrier are similar to those of the freshening composition described herein above, with typically an aqueous carrier at a level of from about 80% to about 99%, preferably from about 85% to about 99%, more preferably from about 90% to about 98% and a freshening perfume at a level of from about 0.001% to about 5%, preferably from about 0.01% to about 1%, more preferably from about 0.05% to about 0.5%, by weight of the cleaning composition. In addition, the cleaning product will contain an effective amount of the cleaning ingredients, especially the enzymes, described hereinbefore, to provide a cleaning effect. The product optionally, but desirably contains the material to control the creation of odor (B) at a level of from about 0.01 to about 5%, preferably from about 0.1% to about 3%, more preferably from about 0.5% to about 2%, and/or the material for absorbing odor (C) disclosed hereinbefore at a level of from about 0.01% to about 5%, preferably from about 0.1% to about 3%, more preferably from about 0.5% to about 2%.

In another preferred cleaning composition, the perfume used is a repellent perfume. This preferred cleaning product provides an aesthetic benefit for humans as well as minimizing odors and stains that would encourage a repeat accident. For cats, the combination of the repellent perfume where the accident occurred and the lack of any such repellent perfume ingredients where the litter is, encourages proper behavior.

As discussed hereinbefore, the present invention comprises a total system in which the component parts work together to provide the desired behavior pattern. Accordingly, the invention comprises kits containing at least two of the behavior control products herein, or one product and the litter herein, but preferably comprises more of the products, up to, and including all of the products and the litter. It also comprises packaging each of the products in association with the instructions for applying the products to provide the desired behavior, e.g., either on the container, or in attached instructions, advertising, etc.

(IV) Article of Manufacture

The above products of the present invention can also be, and are preferably, used in an article of manufacture comprising said composition plus a dispensing means, preferably a spray dispenser.

SPRAY DISPENSER

The article of manufacture herein comprises a spray dispenser. The products are placed into a spray dispenser in order to be distributed onto the desired area, e.g., litter, toys, etc. Said spray dispenser is preferably any of the manually activated means for producing a spray of liquid droplets as is known in the art, e.g. trigger-type, pump-type, non-aerosol self-pressurized, and aerosol-type spray means. The spray dispenser herein preferably does not include those that will substantially foam the products. It is preferred that at least about 80%, more preferably, at least about 90% of the droplets dispensed by the spray dispensers have a particle size of larger than about 30 $\mu$m.

The spray dispenser can be an aerosol dispenser. Said aerosol dispenser comprises a container which can be constructed of any of the conventional materials employed in fabricating aerosol containers. The dispenser must be capable of withstanding internal pressure in the range of from about 20 to about 110 p.s.i.g., more preferably from about 20 to about 70 p.s.i.g. The one important requirement concerning the dispenser is that it be provided with a valve member which will permit the product contained in the dispenser to be dispensed in the form of a spray of very fine, or finely divided, particles or droplets. The aerosol dispenser utilizes a pressurized sealed container from which the product is dispensed through a special actuator/valve assembly under pressure. The aerosol dispenser is pressurized by incorporating therein a gaseous component generally known as a propellant. Common aerosol propellants, e.g., gaseous hydrocarbons such as isobutane, and mixed halogenated hydrocarbons, are not preferred. Halogenated hydrocarbon propellants such as chlorofluoro hydrocarbons have been alleged to contribute to environmental problems. Hydrocarbon propellants can form complexes with the cyclodextrin molecules thereby reducing the availability of uncomplexed cyclodextrin molecules for odor absorption. Preferred propellants are compressed air, nitrogen, inert gases, carbon dioxide, etc. A more complete description of commercially available aerosol-spray dispensers appears in U.S. Pat. No. 3,436,772, Stebbins, issued Apr. 8, 1969; and U.S. Pat. No. 3,600,325, Kaufman et al., issued Aug. 17, 1971; both of said references are incorporated herein by reference.

Preferably the spray dispenser can be a self-pressurized non-aerosol container having a convoluted liner and an elastomeric sleeve. Said self-pressurized dispenser comprises a liner/sleeve assembly containing a thin, flexible radially expandable convoluted plastic liner of from about 0.010 to about 0.020 inch thick, inside an essentially cylindrical elastomeric sleeve. The liner/sleeve is capable of holding a substantial quantity of product and of causing said product to be dispensed. A more complete description of self-pressurized spray dispensers can be found in U.S. Pat. No. 5,111,971, Winer, issued May 12, 1992, and U.S. Pat. No. 5,232,126, Winer, issued Aug. 3, 1993; both of said references are herein incorporated by reference. Another type of aerosol spray dispenser is one wherein a barrier separates the odor absorbing composition from the propellant (preferably compressed air or nitrogen), as disclosed in U.S. Pat. No. 4,260,110, issued Apr. 7, 1981, and incorporated herein by reference. Such a dispenser is available from EP Spray Systems, East Hanover, N.J.

More preferably, the spray dispenser is a non-aerosol, manually activated, pump-spray dispenser. Said pump-spray dispenser comprises a container and a pump mechanism which securely screws or snaps onto the container. The container comprises a vessel for containing the aqueous product to be dispensed.

The pump mechanism comprises a pump chamber of substantially fixed volume, having an opening at the inner end thereof. Within the pump chamber is located a pump stem having a piston on the end thereof disposed for reciprocal motion in the pump chamber. The pump stem has a passageway there through with a dispensing outlet at the outer end of the passageway and an axial inlet port located inwardly thereof.

The container and the pump mechanism can be constructed of any conventional material employed in fabricating pump-spray dispensers, including, but not limited to: polyethylene; polypropylene; polyethyleneterephthalate; blends of polyethylene, vinyl acetate, and rubber elastomer. A preferred container is made of clear, e.g., polyethylene terephthalate. Other materials can include stainless steel. A more complete disclosure of commercially available dispensing devices appears in: U.S. Pat. No. 4,895,279, Schultz, issued Jan. 23, 1990; U.S. Pat. No. 4,735,347, Schultz et al., issued Apr. 5, 1988; and U.S. Pat. No. 4,274,560, Carter, issued Jun. 23, 1981; all of said references are herein incorporated by reference.

Most preferably, the spray dispenser is a manually activated trigger-spray dispenser. Said trigger-spray dispenser comprises a container and a trigger both of which can be constructed of any of the conventional material employed in fabricating trigger-spray dispensers, including, but not limited to: polyethylene; polypropylene; polyacetal; polycarbonate; polyethyleneterephthalate; polyvinyl chloride; polystyrene; blends of polyethylene, vinyl acetate, and rubber elastomer. Other materials can include stainless steel and glass. A preferred container is made of clear, e.g. polyethylene terephthalate. The trigger-spray dispenser does not incorporate a propellant gas into the odor-absorbing composition, and preferably it does not include those that will foam the odor-absorbing composition. The trigger-spray dispenser herein is typically one which acts upon a discrete amount of the product itself, typically by means of a piston or a collapsing bellows that displaces the composition through a nozzle to create a spray of thin liquid. Said trigger-spray dispenser typically comprises a pump chamber having either a piston or bellows which is movable through a limited stroke response to the trigger for varying the volume of said pump chamber. This pump chamber or bellows chamber collects and holds the product for dispensing. The trigger spray dispenser typically has an outlet check valve for blocking communication and flow of fluid through the nozzle and is responsive to the pressure inside the chamber. For the piston type trigger sprayers, as the trigger is compressed, it acts on the fluid in the chamber and the spring, increasing the pressure on the fluid. For the bellows spray dispenser, as the bellows is compressed, the pressure increases on the fluid. The increase in fluid pressure in either trigger spray dispenser acts to open the top outlet check valve. The top valve allows the product to be forced through the swirl chamber and out the nozzle to form a discharge pattern. An adjustable nozzle cap can be used to vary the pattern of the fluid dispensed.

For the piston spray dispenser, as the trigger is released, the spring acts on the piston to return it to its original position. For the bellows spray dispenser, the bellows acts as the spring to return to its original position. This action causes a vacuum in the chamber. The responding fluid acts to close the outlet valve while opening the inlet valve drawing product up to the chamber from the reservoir.

A more complete disclosure of commercially available dispensing devices appears in U.S. Pat. No. 4,082,223, Nozawa, issued Apr. 4, 1978; U.S. Pat. No. 4,161,288, McKinney, issued Jul. 17, 1985; U.S. Pat. No. 4,434,917, Saito et al., issued Mar. 6, 1984; and U.S. Pat. No. 4,819,835, Tasaki, issued Apr. 11, 1989; U.S. Pat. No. 5,303,867, Peterson, issued Apr. 19, 1994; all of said references are incorporated herein by reference.

A broad array of trigger sprayers or finger pump sprayers are suitable for use with the compositions of this invention. These are readily available from suppliers such as Calmar, Inc., City of Industry, Calif.; CSI (Continental Sprayers, Inc.), St. Peters, Mo.; Berry Plastics Corp., Evansville, Ind.—a distributor of Guala® sprayers; or Seaquest Dispensing, Cary, Ill.

The preferred trigger sprayers are the blue inserted Guala® sprayer, available from Berry Plastics Corp., or the Calmar TS800-1A sprayers, available from Calmar Inc., because of the fine uniform spray characteristics, spray volume, and pattern size. Any suitable bottle or container can be used with the trigger sprayer, the preferred bottle is a 17 fl-oz. bottle (about 500 ml) of good ergonomics similar in shape to the Cinch® bottle. It can be made of any materials such as high density polyethylene, polypropylene, polyvinyl chloride, polystyrene, polyethylene terephthalate, glass, or any other material that forms bottles. Preferably, it is made of high density polyethylene or clear polyethylene terephthalate.

For a smaller four fl-oz. size (about 118 ml), a finger pump can be used with canister or cylindrical bottle. The preferred pump for this application is the cylindrical Euromist II®, from Seaquest Dispensing.

(V) Process

Animal litter products according to the present invention can be prepared as follows. The calculated amounts of actives, i.e., antimicrobial and/or urease inhibitor, odor absorbing actives, and optional ingredients, e.g., perfume microcapsules, binders, and the like, are dissolved and/or suspended, in appropriate amounts of liquid carrier, preferably water, enough to sufficiently uniformly distribute the actives over the solid absorbing litter material. All actives are preferably incorporated in the same solution and/or slurry. However, in the cases where the actives are not totally compatibles, such as in the case of cyclodextrin odor control active and an organic urease inhibitor which can form complex with the cyclodextrin, or in the case of a water-insoluble organic antimicrobial which is more effectively soluble in a solvent such as alcohol (and such organic antimicrobial can form complex with the cyclodextrin), it is preferably that the incompatible actives are distributed, e.g., by spraying, sequentially to the animal litter, preferably with a drying step in between. For some absorbing clay litter materials, since the water of the aqueous solutions can be absorbed quickly into the clay particles, the drying step(s) may not be necessary.

For materials with low solubility, such as beta-cyclodextrin, the water is preferably heated to from about 40° C. to about 90° C., preferably from about 50° C. to about 80° C., more preferably from about 60° C. to about 75° C., to permit the use of the minimum amount of water, thus lowering the time and/or heat needed to dry the litter material. Such poorly soluble materials, e.g., beta-cyclodextrin, can also preferably be used in as a finely divided powder and be suspended in a suitable amount of liquid carrier (e.g., preferably, water) into a mobile and sprayable slurry, typically at a liquid carrier-to-powder ratio of from about 1:1 to about 10:1, more preferably from about 2:1 to about 5:1. Similarly, the perfume/cyclodextrin complex is preferably added as a slurry. It is convenient to use the slurry used to form the complex and add any uncomplexed cyclodextrin to that slurry, the excess cyclodextrin helping to make more efficient use of the perfume.

The amount of water necessary will vary with the kind of actives and/or absorbent litter material used and typically is in the range of from about 5 ml to about 500 ml, preferably from about 8 ml to about 250 ml, more preferably from about 12 ml to about 150 ml, per kg of solid absorbing litter material. The amount of solution is preferably just sufficient to distribute the actives on the absorbing litter material. This insures quantitative deposition of the actives and eliminates the necessity of handling excess water. The solid absorbing litter material is then dried at ambient conditions, or in an oven at a temperature of from about 50° C. to about 95° C. This procedure lends itself extremely well to a continuous process, whereby metered flows of solid absorbing litter material and solution (or solutions) and/or slurry (or slurries) of actives are contacted with one another (e.g., by spraying the actives in liquid carriers), and the litter material is subsequently dried on a perforated conveyor belt and/or in an air-dry tunnel. The amount of actives, e.g., antimicrobial/urease inhibitor, odor absorbing actives, perfume, and the like, to be used depends on its effectiveness, its cost and its toxicity.

Mixtures

In general, the more water soluble materials which are added to the animal litter, replenishment compositions, etc., to control the formation of odor and/or absorb odor are desirable to promote spreading. Also, the less toxic materials are more desirable, since animals, and cats, especially, will tend to lick off any litter that sticks to their fur. Mixtures of the above compounds can be used. Mixtures can be more effective and, by limiting the amount of any one material, can be less toxic.

Industrial Process

An animal litter in accordance with the present invention is preferably formed by spraying metered quantities of the slurry onto a quantity of absorbent particles to affix the frangible microcapsules onto at least some of these absorbent particles in substantially intact form. The solutions and/or slurries can be pumped with a conventional metering pump and sprayed through a plurality of conventional spray nozzles onto an evenly distributed bed of absorbent particles being moved, as by a conveyor belt, past the spray nozzles.

The moving bed of absorbent particles is preferably fairly thin, for example about ½" (1.3 cm) to about 1½" (3.8 cm), so that a significant number of the litter particles have affixed actives, and to aid in homogeneous dispersion of the particles with affixed actives in packaging.

All percentages, ratios, and parts herein, in the Specification, Examples, and claims are by weight and are approximations unless otherwise stated. The following are non-limiting examples of the instant composition.

Non-limiting illustrative examples of perfume compositions to be used in the following Examples are as follows:

Perfume A: Freshening perfume for use in animal litter

| Fresh fruity floral | |
|---|---|
| Perfume Ingredients | Wt. % |
| beta gamma Hexenol | 0.3 |
| Cetalox | 0.3 |
| cis-3-Hexenyl salicylate | 2.3 |
| Citral | 3.3 |
| Citronellal nitrile | 2.3 |
| Citronellol | 7.0 |
| Cyclo galbanate | 1.2 |
| Dihydro myrcenol | 5.0 |
| Flor acetate | 10.0 |
| Florhydral | 2.3 |
| Fructone | 9.9 |
| Frutene | 9.9 |
| Galaxolide 50 IPM | 8.4 |
| Geranyl nitrile | 0.7 |
| Helional | 1.3 |
| gamma Methyl ionone | 4.0 |
| Linalool | 4.0 |
| Linalyl acetate | 2.0 |
| Methyl iso butenyl tetrahydro pyran | 0.5 |
| Methyl Phenyl carbinyl acetate | 1.7 |
| Orange oil, cold pressed | 3.3 |
| P.T. Bucinal | 7.0 |
| Phenyl ethyl alcohol | 9.0 |
| Phenyl hexanol | 1.7 |
| Vanillin | 0.7 |
| Verdox | 0.7 |
| Vertocitral | 1.2 |
| Total | 100.0 |

Perfume B: Freshening perfume for use in animal litter

| Woody pine | |
|---|---|
| Perfume Ingredients | Wt. % |
| 4-tertiary Butyl cyclohexyl acetate | 9.24 |
| allo Ocimene | 3.06 |
| Benzyl acetate | 11.51 |
| Citral | 2.44 |
| Citronellol | 5.02 |
| Dihydro myrcenol | 18.36 |
| Eucalyptol | 4.43 |
| Galaxolide 50 IPM | 2.45 |
| Geraniol | 3.18 |
| gamma Methyl ionone | 7.72 |
| Lymolene | 2.06 |
| Methyl iso butenyl tetrahydro pyran | 0.61 |
| Methyl phenyl carbinyl acetate | 1.46 |
| P.T. Bucinal | 1.22 |
| para Cymene | 6.67 |
| Phenyl ethyl acetate | 0.86 |
| Phenyl ethyl alcohol | 8.57 |
| Phenyl ethyl iso butyrate | 4.28 |
| Terpineol | 1.47 |
| Tetrahydro linalool | 4.90 |
| Tetrahydro myrcenol | 0.49 |
| Total | 100.00 |

Perfume C: Freshening perfume for use in animal litter

| Floral (rosy), citrus, fruity | |
|---|---|
| Perfume Ingredients | Wt. % |
| Allyl caproate | 0.5 |
| beta gamma Hexenol | 0.5 |
| Citral | 5.0 |
| Citronellol | 10.0 |
| Eucalyptol | 1.0 |
| Flor acetate | 5.0 |
| Frutene | 3.0 |
| gamma Methyl ionone | 7.0 |
| Geraniol | 30.0 |
| Geranyl acetate | 2.0 |
| Hydroxycitronellal | 15.0 |
| Methyl anthranilate | 2.5 |
| Octyl aldehyde | 0.5 |
| Phenyl ethyl alcohol | 10.0 |
| Phenyl ethyl acetate | 2.0 |
| Terpineol | 5.0 |
| Verdox | 1.0 |
| Total | 100.0 |

Perfume D: Attractant perfume to be sprayed in animal quarters and/or toys.

| Perfume Ingredients | Wt. % |
|---|---|
| 4-tertiary Butyl Cyclohexyl acetate | 4.5 |
| Benzyl acetate | 5.0 |
| cis-3-Hexenyl salicylate | 2.0 |
| Citronellol | 7.0 |
| Citronellyl acetate | 2.5 |
| Coumarin | 3.5 |
| Cyclal C | 1.0 |
| Dihydro myrcenol | 5.0 |
| Dodecalactone | 1.0 |
| Eugenol | 3.0 |
| Flor acetate | 3.8 |
| Frutene | 3.0 |
| Galaxolide 50 IPM | 4.0 |
| Geraniol | 3.0 |
| Geranyl nitrile | 3.0 |
| Hexyl cinnamic aldehyde | 8.0 |
| gamma-Methyl ionone | 7.5 |
| Lauric aldehyde | 2.0 |
| Linalool | 1.5 |
| Linalyl acetate | 2.5 |
| Methyl dihydro jasmonate | 5.5 |
| Methyl iso butenyl tetrahydro pyran | 0.5 |
| Musk plus | 8.0 |
| Nepetalactone | 10.0 |
| Terpineol | 4.0 |
| Undecylenic aldehyde | 0.7 |
| Vanillin | 0.5 |
| Verdox | 1.0 |
| Total | 100.0 |

Perfume E: Freshening deterrent perfume to keep animal away

| Floral Citrus | |
|---|---|
| Perfume Ingredients | Wt. % |
| Anisic aldehyde | 2.0 |
| Benzyl acetate | 3.0 |
| cis-3-Hexenyl acetate | 0.5 |
| Citral | 2.0 |
| Citronella | 2.0 |
| Citronellal nitrile | 3.0 |
| Citronellol | 4.5 |
| Decyl aldehyde | 1.0 |
| Dihydro myrcenol | 10.0 |
| Hexyl cinnamic aldehyde | 8.0 |
| Lemongrass | 1.5 |
| Linalool | 7.0 |
| Methyl beta-naphthyl ketone | 2.0 |
| Methyl dihydro jasmonate | 12.0 |
| Methyl nonyl acetaldehyde | 0.5 |
| Methyl nonyl ketone | 5.0 |
| Orange terpenes | 28.0 |
| Phenyl ethyl alcohol | 5.0 |
| Terpineol | 3.0 |
| Total | 100.0 |

Perfume F: Freshening deterrent perfume to keep animal away

| Wintergreen | |
|---|---|
| Perfume Ingredients | Wt. % |
| alpha-Pinene | 1.0 |
| Amyl Salicylate | 15.0 |
| Anisic aldehyde | 2.0 |
| beta-Pinene | 1.0 |
| Cinnamic alcohol | 2.0 |
| Cinnamic alhehyde | 0.5 |
| Dihydro myrcenol | 10.0 |
| Dodecalactone | 0.5 |
| Eucalyptol | 3.0 |
| Eugenol | 1.0 |
| Hexyl cinnamic aldehyde | 5.0 |
| Hexyl salicylate | 4.0 |
| laevo-Carvone | 1.0 |
| Lemongrass | 1.0 |
| Linalool | 5.0 |
| Menthol | 2.0 |
| Methyl benzoate | 1.5 |
| Methyl nonyl acetaldehyde | 0.5 |
| Methyl nonyl ketone | 10.0 |
| Methyl salicylate | 20.0 |
| Orange terpenes | 10.0 |
| Terpineolene | 2.0 |
| Thymol | 2.0 |
| Total | 100.0 |

Following are non-limiting examples of moisture-activated encapsulated perfunes (cyclodextrin/perfilme inclusion complexes and matrix perfume microcapsules) that can be incorporated into the animal litter of this invention.

Complex 1

A mobile slurry is prepared by mixing about 1 kg of beta-cyclodextrin and about 1,000 ml of water in a stainless steel mixing bowl of a KitchenAid® mixer using a plastic coated heavy duty mixing blade. Mixing is continued while about 175 g of perfume is slowly added. The liquid-like slurry immediately starts to thicken and becomes a creamy paste. Stirring is continued for about 30 minutes. About 500 ml of water is added to the paste and blended well. Stirring is then resumed for about an additional 30 minutes. The resulting creamy complex is spread in a thin layer on a tray and allowed to air dry. This produces about 1.1 kg of granular solid which is ground to a fine powder. The dry powder can also be further freeze-dried into a fine powder. Examination of the complex particles by scanning electron microscopy shows that practically all of the ultimate (primary) particles of the complex have particle sizes less than about 5 microns.

For commercial production, the creamy complex can also be heat dried such as in a rotary drum dryer. Complex 1 can be applied to the animal litter by uniformly sprinkling, mixing, or distributing the complex particles onto the solid liquid-absorbent litter material.

Slurry 1

A mobile slurry is prepared by mixing about 600 g of beta-cyclodextrin and 600 ml of water in a stainless steel mixing bowl of a KitchenAid® mixer using a plastic coated heavy duty mixing blade. Mixing is continued while about 105 g of the perftume is slowly added. The liquid-like slurry immediately starts to thicken and becomes a creamy paste. Stirring is continued for about 30 minutes. About 1,200 ml of water is slowly added to the slurry with stirring. The stirring continues for about an additional 10 minutes to give a liquid Slurry 1. Slurry 1 can be applied to the animal litter by uniformly spraying the mobile slurry onto the solid liquid-absorbent litter material followed by a drying step.

Slurry 2

A mobile slurry is prepared similar to that of Slurry 1 except that the additional 1,200 ml of water contains about 20 g of dissolved polyethylene glycol with molecular weight of about 3,400. The stirring continues for about an additional 10 minutes to give a liquid Slurry 2. Slurry 2 can be applied to the animal litter by uniformly spraying the mobile slurry onto the solid liquid-absorbent litter material followed by a drying step.

Mixed Perfume Complex/Cyclodextrin Slurry 1 beta-Cyclodextrin powder is obtained by grinding beta-cyclodextrin crystals in a Trost Air Impact Pulverizer jet mill. The powder has an average particle size of about 5 microns. A mobile slurry is prepared by mixing about 200 g of the beta-cyclodextrin powder in about 800 ml of water in a stainless mixing bowl of a KitchenAid® mixer using a plastic coated heavy duty mixing blade. Mixing is continued while about 50.1 g of cyclodextrin/perfume complex Slurry 1 is added. Stirring is continued for about 5 minutes to yield the mixed perfume complex/cyclodextrin Slurry 1. The mixed perfume complex/cyclodextrin Slurry 1 can be applied to the animal litter by uniformly spraying the mobile slurry onto the solid liquid-absorbent litter material followed by a drying step.

Mixed Perfume Complex/Cyclodextrin Slurry 2

A mobile slurry is prepared similar to that of the mixed perfume complex/cyclodextrin Slurry 1, except that about 10 g of polyethylene glycol with molecular weight of about 4,600 is dissolved in the cyclodextrin slurry before the addition of the cyclodextrin/perfume complex slurry. The mixed perfume complex/cyclodextrin Slurry 2 can be applied to the animal litter by uniformly spraying the mobile slurry onto the solid liquid-absorbent litter material followed by a drying step.

Complex Particles 1

Solid cyclodextrin/perfume complex/polyethylene glycol particles are prepared as follows. One part of Complex 1 is mixed thoroughly with about 2 part of molten polyethylene glycol with an average molecular weight of about 3,400, at about 70° C. The composition solidifies upon cooling, and is cryogenically ground in dry ice. The resulting solid cyclodextrin/perfume complex/polyethylene glycol particles are sorted to get particle size of less than about 500 microns. Complex Particles 1 can be applied to the animal litter by uniformly sprinkling, mixing, or distributing the complex particles onto the solid liquid-absorbent litter material and the resulting mixture is heated to about 80° C. for 5 minutes in an oven or under infrared light to attached said Complex Particles 1 onto said animal litter material.

Complex Particles 2

Solid cyclodextrin/perftume complex/polyethylene glycol particles are prepared as follows. One part of Complex 1 is mixed thoroughly with about 3 part of molten polyethylene glycol with an average molecular weight of about 1,450, at about 80° C. The molten composition is atomized in a spray drying tower to obtain solid particles. Solid particles solidify on the wall of the tower and are removed for particle size classification. Particles larger than about 500 microns are ground further to reduce the particle size by cryogenic grinding with dry ice. Complex Particles 2 can be applied to the animal litter by uniformly sprinkling, mixing, or distributing the complex particles onto the solid liquid-absorbent litter material and the resulting mixture is heated to about 80° C. for 5 minutes in an oven or under infrared light to attached said Complex Particles 1 onto said animal litter material.

Moisture-Activated Matrix Perfume Microcansules

Moisture-activated matrix perfume microcapsules can be applied to the animal litter by uniformly sprinkling, mixing, or distributing the microcapsules onto the solid liquid-absorbent litter material. An example of water-activated matrix perfume microcapsules is made according to Example 1 of U.S. Pat. No. 3.971,852, having a perfume loading of about 60%.

All percentages, ratios, and parts herein, in the Specification, Examples, and claims are by weight and are approximations unless otherwise stated.

The following are non-limiting examples of the instant compositions, articles. and methods.

Two samples of commercial clay cat litter products are used in the following non-limiting animal litter compositions of the present invention. One product is the Unscented Ever Clean® Premium Clumping Litter, Extra Strength for Multiple Cats, a clumping clay product from A&M Products, a First Brands Company, Danbury, Conn. The Unscented Ever Clean Premium Clumping Litter is used as is. The other product is Sophista-Cat® Cat Litter, a simple ground clay product from Pacific Coast Distributing, Inc., Phoenix, Ariz. The unscented Sophista-Cat ground clay is further sieved through Sieve #7 (2.80 mm) and retained on Sieve #10 (2 mm) for use in the preparation of the animal litter compositions.

| Ingredients | Ex. I Wt. % | Ex. II Wt. % | Ex. III Wt. % | Ex. IV Wt. % |
|---|---|---|---|---|
| Hydroxypropyl beta-cyclodextrin | 0.73 | 0.36 | 0.73 | 0.36 |
| Zinc chloride | 0.73 | 0.36 | 0.73 | 0.36 |
| Ground clay litter material[a] | Balance | Balance | — | — |
| Clumping clay litter material[b] | | | Balance | Balance |

[a]Sophista-Cat ground clay, particle size from about 2 mm to about 2.8 mm.
[b]Ever Clean clumping clay.

EXAMPLE I

About 7 parts of an aqueous solution of hydroxypropyl beta-cyclodextrin (approximately 40% active) is blended with about 4 parts of an aqueous solution of zinc chloride (approximately 70% active) to form a mixed concentrated cyclodextrin-zinc chloride solution which contains about 25.45% hydroxypropyl beta-cyclodextrin and about 25.45% zinc chloride. About 57.36 g of the mixed cyclodextrin-zinc chloride solution is sprayed uniformly with frequent mixing onto about 2,000 g of Sophista-Cat ground clay, and let dry to obtain the animal litter composition of Example I.

EXAMPLE II

The composition of Example II is prepared similarly to the procedure of Example I, except that only about 28.68 g of the mixed cyclodextrin-zinc chloride solution is sprayed onto about 2,000 g of Sophista-Cat ground clay.

EXAMPLES III and IV

The compositions of Examples III and IV are prepared similarly to the procedure of Examples I and II, respectively, except that the Ever Clean clumping clay is used instead of the Sophista-Cat ground clay.

| | Comparative Example V Wt. % | Comparative Example VI Wt. % |
|---|---|---|
| Hydroxypropyl beta-cyclodextrin | 1.46 | — |
| Zinc chloride | — | 1.46 |
| Ground clay litter material | Balance | Balance |

COMPARATIVE EXAMPLE V

The composition of Comparative Example V is prepared similarly to the procedure of Example I, except that about 73 g of the hydroxypropyl beta-cyclodextrin aqueous solution (approximately 40% active) is sprayed onto about 2,000 g of Sophista-Cat ground clay.

COMPARATIVE EXAMPLE VI

The composition of Comparative Example VI is prepared similarly to the procedure of Example I, except that about 41.74 g of the zinc chloride aqueous solution (approximately 70% active) is sprayed onto about 2,000 g of Sophista-Cat ground clay.

The product is evaluated for odor control by placing about 3 pounds (about 1,362 g) of product in a cat litter tray in homes which have 2 to 4 cats. The feces is removed daily. At the end of the third day, malodor level of the litter tray is graded. It is found that animal litter of Example I has noticeable lower malodor than the untreated animal litter as well as having noticeable lower malodor than those of Comparative Examples V and VI.

| Ingredients | Ex. VII Wt. % | Ex. VIII Wt. % | Ex. IX Wt. % |
|---|---|---|---|
| Hydroxypropyl beta-cyclodextrin | 0.18 | 0.09 | 0.27 |
| Zinc chloride | 0.18 | 0.27 | 0.09 |
| Clumping clay litter material | Balance | Balance | Balance |

| Ingredients | Ex. X Wt. % | Ex. XI Wt. % | Ex. XII Wt. % | Ex. XIII Wt. % |
|---|---|---|---|---|
| Methylated beta-cyclodextrin | 0.36 | 0.18 | 0.54 | 0.18 |
| Zinc chloride | 0.36 | 0.54 | 0.18 | 0.18 |
| Ground clay litter material | Balance | Balance | Balance | Balance |

| Ingredients | Ex. XIV Wt. % | Ex. XV Wt. % | Ex. XVI Wt. % | Ex. XVII Wt. % |
|---|---|---|---|---|
| beta-Cyclodextrin | 0.36 | 0.18 | 0.54 | 0.18 |
| Zinc chloride | 0.36 | 0.54 | 0.18 | 0.18 |
| PEG(c) | — | — | 0.03 | 0.03 |
| Ground clay litter material | Balance | Balance | Balance | — |
| Clumping clay litter material | | | | Balance |

(c)Polyethylene glycol of average molecular weight of about 4,600.

EXAMPLE XIV beta-Cyclodextrin powder is obtained by grinding beta-cyclodextrin crystals in a Trost Air Impact Pulverizer jet mill. The powder has an average particle size of about 5 microns. A mobile slurry is prepared by mixing about 200 g of the beta-cyclodextrin powder in about 800 ml of water in a stainless mixing bowl of a KitchenAid® mixer using a plastic coated heavy duty mixing blade. Mixing is continued while about 285.7 g of a zinc chloride aqueous solution (approximately 70% active) is added. Stirring is continued for about 5 minutes to yield the mixed cyclodextrin and zinc chloride slurry. About 46.29 g of the mixed slurry is applied to the animal litter by uniformly spraying the mobile slurry onto about 2,000 g of solid liquid-absorbent litter material, followed by a drying step, to obtain the animal litter composition of Example XIV.

EXAMPLE XV

The litter composition of Example XV is prepared similarly to that of Example XIV using the appropriate amounts of actives.

EXAMPLE XVI

A mobile slurry is prepared by mixing about 200 g of the beta-cyclodextrin powder and about 11 g of a polyethylene glycol with an average molecular weight of about 4,600 in about 800 ml of water, in a stainless mixing bowl of a KitchenAid® mixer using a plastic coated heavy duty mixing blade. Mixing is continued while about 95.24 g of a zinc chloride aqueous solution (approximately 70% active) is added. Stirring is continued for about 5 minutes to yield the mixed cyclodextrin and zinc chloride slurry. About 59.74 g of the mixed slurry is applied to the animal litter by uniformly spraying the mobile slurry onto about 2,000 g of solid liquid-absorbent litter material, followed by a drying step, to obtain the animal litter composition of Example XVI.

EXAMPLE XVII

The litter composition of Example XVII is prepared similarly to that of Example XVI using the appropriate amounts of actives.

| Ingredients | Ex. XVIII Wt. % | Ex. XIX Wt. % | Ex. XX Wt. % | Ex. XXI Wt. % |
|---|---|---|---|---|
| beta-Cyclodextrin | 0.40 | 0.50 | — | — |
| Hydroxypropyl-beta-cyclodextrin | — | — | 0.36 | 0.40 |
| Zinc chloride | 0.30 | 0.20 | — | — |
| 2,4,5-Trichlorophenol | — | 0.01 | — | — |
| Bronopol | — | — | 0.03 | — |
| Chlorhexidine | — | — | — | 0.05 |
| Ground clay litter material | Balance | Balance | Balance | Balance |

EXAMPLE XVIII

A warm solution is prepared by mixing about 1 part of the beta-cyclodextrin in about 9 parts of water maintained at a temperature of about 70° C., in a stainless vessel. About 80 g of the warm solution is applied to the animal litter by uniformly spraying the solution, with frequent mixing, onto about 2,000 g of ground clay litter material and let dry. About 15 g of a aqueous zinc chloride solution (about 40% active) is then uniformly sprayed, with mixing, onto the litter material, to obtain the animal litter composition of Example XVIII.

EXAMPLE XIX

The litter composition of Example XIX is prepared similarly to that of Example XVIII using the appropriate amounts of beta-cyclodextrin and zinc chloride, followed by spraying of about 20 g of an aqueous solution (about 1% active) of trichlorophenol.

EXAMPLES XX and XXI

The litter compositions of Examples XX and XXI are prepared by sequential spraying of appropriate amounts of a hydroxypropyl-beta-cyclodextrin solution and a antimicrobial solution.

| Ingredients | Ex. XXII Wt. % | Ex. XXIII Wt. % | Ex. XXIV Wt. % | Ex. XXV Wt. % |
|---|---|---|---|---|
| beta-Cyclodextrin | 0.40(f) | 0.50(g) | — | — |
| Hydroxypropyl-beta-cyclodextrin | — | — | 0.36 | — |
| Methylated beta-cyclodextrin | — | — | — | 0.40 |
| Trichlorocarbanilide | 0.20 | 0.10 | — | — |
| Diaminophosphoric acid ester UI(d) | — | 0.03 | — | — |
| Phthalic anhydride urease inhibitor | — | — | 0.08 | — |
| Hydroxamic acid derivative UI(e) | — | — | — | 0.06 |
| Cyclodextrin/perfume complex | 0.0282(f) | 0.05(g) | 0.071(h) | — |
| Perfume Complex Particles 1 | — | — | — | 0.127 |
| PEG-4600 | 0.02(f) | 0.025(g) | — | — |
| Ground clay litter material | Balance | Balance | — | — |
| Clumping clay litter material | — | — | Balance | Balance |

(d)Diaminophosphoric acid phenyl ester urease inhibitor.
(e)Naphthyloxy-alkane-hydroxamic acid urease inhibitor
(f)A slurry containing beta-cyclodextrin, cyclodextrin/Perfume A complex and polyethylene glycol of average MW of about 4600, prepared as the Mixed Perfume Complex/Cyclodextrin Slurry 2 given hereinbefore; the concentration of Perfume A in the litter composition is about 0.0042%.
(g)The slurry used is similar to that of Example XXII, with higher levels of beta-cyclodextrin, cyclodextrin/Perfume B complex and PEG.
(h)About 0.251% of Slurry 1, prepared with Perfume C is used to provide about 0.071% cyclodextrin/Perfume C complex.

EXAMPLE XXII

An aqueous slurry containing beta-cyclodextrin, cyclodextrin/Perfume A complex and polyethylene glycol of average MW of about 4600 is prepared according to the procedure of Mixed Perfume Complex/Cyclodextrin Slurry 2 given hereinabove. About 42.4 g of the slurry is applied to the animal litter by uniformly spraying the mobile slurry onto about 2,000 g of solid liquid-absorbent litter material, followed by a spraying of a 5% ethanolic solution of 3,4,4'-trichlorocarbanilide, and a drying step, to obtain the animal litter composition of Example XXII.

EXAMPLE XXIII

An aqueous slurry containing beta-cyclodextrin, cyclodextrin/Perfume B complex and polyethylene glycol of average MW of about 4600 is prepared similar to the procedure of Mixed Perfume Complex/Cyclodextrin Slurry 2 given hereinabove. An ethanolic solution containing about 10% 3,4,4'-trichlorocarbanilide and about 3% diaminophosphoric acid phenyl ester urease inhibitor, as disclosed in DD 241,012, Nov. 26, 1986, is prepared separately. The cyclodextrin slurry is first applied to the animal litter by spraying, followed by a spraying of the ethanolic solution, and a drying step, to obtain the animal litter composition of Example XXIII.

EXAMPLE XXIV

The animal litter composition of Example XXIV is prepared by a successive spraying of an aqueous solution of the cyclodextrin derivative, a solution of the urease inhibitor, and a slurry of beta-cyclodextrin/Perfume C complex which is prepared according to the procedure of the Slurry 1 given hereinabove.

EXAMPLE XXV

The animal litter composition of Example XXV is prepared by a successive spraying of an aqueous solution of the cyclodextrin derivative and a solution of the urease inhibitor, followed by a drying step. The naphthyloxy-alkane-hydroxamic acid urease inhibitor is prepared according to DD 149,505, Jul. 15, 1981, with n=2. A suitable amount of cyclodextrin/perfume A complex, coated by polyethylene glycol, prepared according to the Complex Particles 2 given hereinbefore, is uniformly blended with the animal litter material, then the resulting composition is heated to melt the polyetlylene glycol and to bind the cyclodextrin complex to the litter material.

| Ingredients | Ex. XXVI Wt. % | Ex. XXVII Wt. % | Ex. XXVIII Wt. % | Ex. XXIX Wt. % |
|---|---|---|---|---|
| Hydroxypropyl-beta-cyclodextrin | 0.30 | — | — | — |
| Hydroxypropyl-alpha-cyclodextrin | 0.13 | — | — | — |
| Propylene glycol | 0.03 | — | — | — |
| beta-Cyclodextrin | — | 0.20 | — | — |
| Abscents | — | — | 2.0 | — |
| Zeolite | — | — | — | 3.0 |
| Zinc chloride | 0.15 | 0.20 | 0.30 | 0.05 |
| Cyclodextrin/perfume complex | 0.05(j) | — | 0.07(k) | — |
| PEG-4600 | 0.002 | — | 0.002 | — |
| Moisture-activated microcapsules | — | 0.015(j) | — | — |
| Pressure-activated microcapsules | — | — | — | 0.05(l) |
| Cellulosic litter material | Balance | — | — | — |
| Mixed Clay/Cellulosic litter material | — | Balance | — | — |

-continued

| Ingredients | Ex. XXVI Wt. % | Ex. XXVII Wt. % | Ex. XXVIII Wt. % | Ex. XXIX Wt. % |
|---|---|---|---|---|
| Ground clay litter material | | | Balance | — |
| Clumping clay litter material | | | | Balance |

(j)The cyclodextrin/perfume complex is prepared according to the procedure of Slurry 2 given hereinabove, using beta-cyclodextrin, Perfume A, and polyethylene glycol with an average MW of about 4,600. About 0.179% of Slurry 2 is needed to provide about 0.05% of cyclodextrin/perfume complex.
(j)The water-activated matrix perfume microcapsules is prepared according to Example 1 of U.S. Pat. No. 3,971,852, using Perfume B; the capsules have a perfume loading of about 60%.
(k)The cyclodextrin/perfume complex is prepared according to the procedure of Slurry 2 given hereinabove, using beta-cyclodextrin, Perfume C, and polyethylene glycol with an average MW of about 4,600. About 0.25% of Slurry 2 is needed to provide about 0.07% of cyclodextrin/perfume complex.
(l)The pressure-activated matrix perfume microcapsules is prepared according to U.S. Pat. No. 4,407,231, Colborn et al, issued Oct. 4, 1983, using Perfume A; the capsules have a perfume loading of about 65%.

The surfactant for use in cleaning and/or in solubilizing the preferred perfumes in aqueous compositions containing cyclodextrins is preferably cyclodextrin-compatible, that is it should not substantially form a complex with the cyclodextrin so as to diminish performance of the cyclodextrin and/or the surfactant. Complex formation diminishes both the ability of the cyclodextrin to absorb odors and the ability of the surfactant to solubilize the perfumes in the aqueous compositions.

Nonlimiting examples of cyclodextrin-compatible nonionic surfactants include block copolymers of ethylene oxide (EO) and propylene oxide (PO), polyalkyleneoxide polysiloxanes. and alkyldiphenyl oxide disulfonates. Nonlimiting examples of cyclodextrin-compatible EO/PO surfactants are Pluronic® and Tetronic®. Examples of polyalkyleneoxide polysiloxanes are the Silwet® surfactants which are available from OSi Specialties, Inc., Danbury, Conn. Examples of alkyldiphenyl oxide disulfonate surfactants are sold under the name Dowfax®, and are available from the Dow Chemical Company.

Following are nonlimiting Examples of compositions and articles of manufacture for use to repel animals.

| Ingredients | Ex. XXX Wt. % | Ex. XXXI Wt. % | Ex. XXXII Wt. % | Ex. XXXIII Wt. % | Ex. XXXIV Wt. % | Ex. XXXV Wt. % |
|---|---|---|---|---|---|---|
| Methylated beta-cyclodextrin | — | — | 1 | — | — | — |
| Hydroxypropyl beta-cyclodextrin | — | — | — | 1 | — | 1 |
| Zinc chloride | — | 1 | 1 | 1 | — | 1 |
| Perfume E | 0.05 | — | 0.01 | — | — | 0.1 |
| Perfume F | — | 0.1 | — | 0.1 | 0.07 | — |
| Polysorbate 60 | 0.07 | — | — | — | 0.1 | — |
| Pluronic P84 | — | — | 0.1 | — | — | 0.1 |
| Silwet L-7600 | — | 0.1 | — | 0.1 | — | — |
| Papain | — | — | — | — | 0.01 | — |
| PEG-Subtilisin | — | — | — | — | — | 0.001 |
| Kathon CG | — | — | 0.0008 | 0.0008 | 0.0005 | 0.0008 |
| HCl | * | * | * | * | — | * |
| Distilled Water | Balance | Balance | Balance | Balance | Balance | Balance |

* To adjust pH to about 4.0.

EXAMPLE XXXVI

The composition of Example XXX is loaded into a blue inserted Guala® trigger sprayer, available from Berry Plastics Corp., said sprayer comprising instructions to spray said composition onto areas to keep animals away from said areas, and then, in accordance with said instructions, the composition is sprayed onto a clothed sofa, and allowed to evaporate off the sofa.

EXAMPLE XXXVII

The composition of Example XXXII is loaded into a cylindrical Euromist II® pump sprayer available from Seaquest Dispensing, said sprayer comprising instructions to spray said composition onto areas to keep animals away from said areas, and then, in accordance with said instructions, the composition is sprayed onto draperies, and allowed to evaporate off the draperies.

EXAMPLE XXXVIII

The compositions of Example XIII is loaded into a Calmar TS800-1A trigger sprayer, available from Calmar Inc., said sprayer comprising instructions to spray said composition onto areas to keep animals away from said areas, and then, in accordance with said instructions, the composition is sprayed onto a carpet, and allowed to evaporate off the carpet.

Following are nonlimiting Examples of compositions and articles of manufacture for use to attract animals.

| Ingredients | Ex. XXXIX Wt. % | Ex. XXXX Wt. % | Ex. XXXXI Wt. % | Ex. XXXXII Wt. % | Ex. XXXXIII Wt. % | Ex. XXXXIV Wt. % |
|---|---|---|---|---|---|---|
| Methylated beta-cyclodextrin | — | — | 1 | — | — | — |
| Hydroxypropyl beta-cyclodextrin | — | — | — | 1 | — | 1 |
| Zinc chloride | — | 1 | 1 | 1 | — | 1 |
| Perfume D | 0.05 | 0.05 | 0.07 | 0.1 | 0.07 | 0.1 |
| Polysorbate 60 | 0.07 | — | — | — | 0.1 | — |
| Pluronic P84 | — | — | 0.1 | — | — | — |
| Silwet L-7600 | — | 0.1 | — | 0.1 | — | 0.1 |
| Papain | — | — | — | — | 0.01 | — |
| PEG-Subtilisin | — | — | — | — | — | 0.001 |
| Kathon CG | — | — | 0.0008 | 0.0008 | — | 0.0008 |
| HCl | — | * | * | * | — | * |
| Distilled Water | Balance | Balance | Balance | Balance | Balance | Balance |

* To adjust pH to about 4.0.

EXAMPLE XXXXV

The composition of Example XXXX is loaded into a blue inserted Guala® trigger sprayer, available from Berry Plastics Corp., said sprayer comprising instructions to spray said composition onto areas to attract animals to said areas, and then, in accordance with said instructions, the composition is sprayed onto an animal bed, and allowed to evaporate off the bed.

EXAMPLE XXXXVI

The composition of Example XXXXII is loaded into a cylindrical Euromist II® pump sprayer available from Seaquest Dispensing, said sprayer comprising instructions to spray said composition onto areas to keep animals away from said areas, and then in accordance with said instructions, the composition is sprayed onto a scratching post, and allowed to evaporate off the scratching post.

EXAMPLE XXXXVII

The compositions of Example XXXXIII is loaded into a Calmar TS800-1A trigger sprayer, available from Calmar Inc., said sprayer comprising instructions to spray said composition onto areas to keep animals away from said areas, and then, in accordance with said instructions, the composition is sprayed onto a carpet, and allowed to evaporate off the carpet.-

Following are nonlimiting Examples of freshening compositions and articles of manufacture for use to control animal odor.

| Ingredients | Ex. XXXXVIII Wt. % | Ex. XXXXIX Wt. % | Ex. L Wt. % | Ex. LI Wt. % | Ex. LII Wt. % | Ex. LIII Wt. % |
|---|---|---|---|---|---|---|
| Methylated beta-cyclodextrin | — | — | 1 | — | 1.2 | — |
| Hydroxypropyl beta-cyclodextrin | — | — | — | 1 | — | 1 |
| Zinc chloride | — | 1 | 1 | 1 | — | 1 |
| Perfume A | 0.05 | — | — | 0.1 | — | — |
| Perfume B | — | 0.1 | — | — | 0.07 | — |
| Perfume C | — | — | 0.1 | — | — | 0.1 |
| Polysorbate 60 | — | 0.1 | — | — | 0.1 | — |
| Pluronic P84 | — | — | 0.1 | — | — | — |
| Silwet L-7600 | 0.1 | — | — | 0.1 | — | 0.1 |
| Chlorhexidine | 0.03 | — | — | — | — | 0.05 |
| Papain | — | — | 0.01 | — | 0.01 | — |
| PEG-Subtilisin | — | — | — | — | — | 0.001 |
| Kathon CG | — | — | 0.0005 | 0.0005 | 0.0008 | 0.0005 |
| HCl | — | * | * | * | — | * |
| Distilled Water | Balance | Balance | Balance | Balance | Balance | Balance |

* To adjust pH to about 4.0.

EXAMPLE LIV

The composition of Example XXXXIX is loaded into a cylindrical Euromist II® pump sprayer available from Seaquest Dispensing, said sprayer comprising instructions to spray said composition on to areas where animals have caused, or may cause, an odor to freshen said areas, and then, in accordance with said instructions, the composition is sprayed onto a dry carpet that is previously soiled with animal's urine, and allowed to evaporate off the carpet.

EXAMPLE LV

The composition of Example LII is loaded into a blue inserted Guala® trigger sprayer, available from Berry Plastics Corp., said sprayer comprising instructions to spray said composition on to areas where animals have caused, or may cause, an odor to freshen said areas, and then, in accordance with said instructions, the composition is sprayed onto a floor area surrounding an animal litter tray, and allowed to evaporate off the floor.

EXAMPLE LVI

The compositions of Example VIII is loaded into a Calmar TS800-1A trigger sprayer, available from Calmar Inc., said sprayer comprising instructions to spray said composition on to areas where animals have caused, or may cause, an odor to freshen said areas, and then, in accordance with said instructions, the composition is sprayed onto a soiled animal litter, and allowed to evaporate off the litter.

EXAMPLE LVII

The composition of Example L is loaded into a plastic bottle, said bottle comprising instructions to apply said composition onto areas where animals have caused, or may cause, an odor to freshen said areas, and then, in accordance with said instructions, the composition is poured from the bottle onto a dry carpet that is previously soiled with animal's urine, and allowed to evaporate off the carpet. Following are nonlimiting Examples of cleaning compositions and articles of manufacture for use to clean animal excretions.

| Ingredients | Ex. LVIII Wt. % | Ex. LIX Wt. % | Ex. LX Wt. % | Ex. LXI Wt. % | Ex. LXII Wt. % |
|---|---|---|---|---|---|
| Methylated beta-cyclo-dextrin | — | — | — | 1.2 | — |
| Hydroxypropyl beta-cyclodextrin | — | — | 1 | — | 1 |
| Zinc chloride | — | 1 | 1 | — | — |
| Perfume A | — | 0.05 | — | — | — |
| Perfume B | — | — | — | 0.07 | — |
| Perfume C | — | — | — | — | 0.1 |
| Perfume E | 0.1 | — | — | — | — |
| Perfume F | — | — | 0.1 | — | — |
| Isopropanol | 3 | — | 3 | 3 | 3 |
| Propylene Glycol | 6 | — | — | — | 3 |
| Sodium Alkyl Sulfate (~$C_{13}$) | 0.25 | — | — | — | — |
| Pluronic P84 | — | — | 0.25 | — | — |
| Silwet L-7600 | — | 0.25 | — | 0.25 | 0.25 |
| Chlorhexidine | — | 0.05 | — | — | 0.05 |
| Savinase* | 0.0005 | — | — | 0.0005 | — |
| Papain | — | 0.01 | — | — | — |
| PEG-Subtilisin | — | — | — | — | 0.001 |
| Kathon CG | — | 0.0005 | 0.0005 | 0.0008 | 0.0005 |
| HCl | — | ** | ** | — | — |
| NaOH | *** | — | — | — | — |
| Distilled Water | Balance | Balance | Balance | Balance | Balance |

*A protease available from Novo Industries A/S (Denmark).
** To adjust pH to about 4.0.
*** To adjust pH to about 11.

The composition of Example LVIII is loaded into a cylindrical Euromist II® pump sprayer available from Seaquest Dispensing, said sprayer comprising instructions to spray said composition onto areas where animals have made a mess as part of a cleaning process. A carpet is soiled with animal's feces. The solid soil is removed and the soiled area is wiped with paper towels. The composition of Example LVIII is then sprayed on the soiled area in accordance with said instructions, and then wiped off with paper towels and allowed to dry.

EXAMPLE LXIV

The composition of Example LIX is loaded into a blue inserted Guala® trigger sprayer, available from Berry Plastics Corp, said sprayer comprising instructions to use said composition on animal soils to assist in their removal. A carpet is soiled with animal's vomit. The solid soil is removed and the soiled area is wiped with paper towels. The composition of Example LIX is then sprayed, in accordance with said instructions, on the soiled area, and wiped off with paper towels and allowed to dry.

EXAMPLE LXV

The compositions of Example LX is loaded into a Calmar TS800-1A trigger sprayer, available from Calmar Inc. A carpet is soiled with animal's urine. The soiled area is wiped with paper towels. The composition of Example LX is then sprayed on the soiled area, and wiped off with paper towels and allowed to dry.

EXAMPLE LXVI

The composition of Example LXI is loaded into a blue inserted Guala® trigger sprayer, available from Berry Plastics Corp. A linoleum floor is soiled with animal's feces. The solid soil is removed and the soiled area is wiped with paper towels. The composition of Example LXI is then sprayed on the soiled area, and wiped off with paper towels and allowed to dry.

EXAMPLE LXVII

The composition of Example LXII is loaded into a cylindrical Euromist II® pump sprayer available from Seaquest Dispensing. A car seat is soiled with animal's saliva. The soiled area is first wiped with paper towels. The composition of Example LXII is then sprayed on the soiled area, and wiped off with paper towels and allowed to dry.

Following are nonlimiting Examples of concentrated freshening compositions to be applied to fresh animal litters:

EXAMPLE LXVIII

An aqueous composition comprising about 200 g of beta-cyclodextrin, about 200 g of zinc chloride, about 1.5 g of perfume A, and about 900 g of water is prepared according to the procedure of Example XIV and packaged in association with instructions to apply said composition uniformly to absorbent animal litter material to prepare a litter that minimizes odor. This composition is used in accordance with said instructions and is sprayed uniformly, with sufficient mixing to provide uniform distribution, on fresh solid litter material in a litter tray at a level of from about 10 g to about 80 g of composition per 1000 g of litter material.

EXAMPLE LXIX

An aqueous composition comprising about 50 g hydroxypropyl beta-cyclodextrin, about 100 g of zinc chloride, about 1 g perfume B, about 1 g of Silwet L-7600 surfactant, about 0.5 g of chlorhexidine, and about 850 g of water is prepared by mixing the ingredients together. This composition is used to spray uniformly, with sufficient mixing to provide uniform distribution, on fresh solid litter material in a litter tray at a level of from about 20 g to about 100 g of composition per 1000 g of litter material.

What is claimed is:

1. Composition for animal care selected from the group consisting of:
   (I) solid liquid-absorbing litter composition, that is useful as animal litter, comprising: (1) solid liquid absorbing litter material; (2) an effective amount of material that inhibits the formation of odor that has at least one attribute selected from the group consisting of antimicrobial activity, urease inhibition activity, pH adjustment activity, proteolytic activity, and mixtures thereof; and also, (3) an effective amount of odor absorbing material for controlling objectionable odor molecules;
   (II) aqueous freshening composition for animal litter as in (I), said aqueous freshening composition comprising:
      (A) an effective amount of refreshing perfume containinig a substantial amount of perfume ingredients that provide a freshness impression to humans and which does not contain effective amounts of either animal repellent perfume ingredients or animal attractant perfume ingredients;
      (B) an effective amount of a material to inhibit the formation of odor and has at least one attribute selected from the group consisting of: urease inhibition activity, pH adjustment activity, proteolytic activity, and mixtures thereof;
      (C) optionally, odor absorbing material for controliig objectionable odor molecules;
      (D) optionally. solubilizing and/or suspension aid and/ or solvent; and
      (E) aqueous carrier; said composition being packaged in association with instructions to apply it in an effective amount to animal litter and/or surfaces that are affected by animal odors;
   (III) aqueous animal repellent composition comprising:
      (A) an effective amount of repellent perfume containing at least about 40% of animal repellent perfume ingredients and, optionally, a substantial amount of non-repellent perfume ingredients that provide a freshness impression to humans, and, if the perfume does not contain said non-repellent perfume ingredients, there being at least four repellent perfume ingredients;
      (B) optionally, an effective amount of a material selected from the group consisting of: (1) material to hillbit the formation of odor and has at least one attribute selected from the group consisting of: antimicrobial activity, urease inhibition activity, pH adjustment activity, proteolytic activity, and mixtures thereof; (2) odor absorbing material for controlling objectionable odor molecules; and (3) mixtures thereof;
      (C) optionally, solubilizing and/or suspension aid and/ or solvent; and
      (D) aqueous carrier;
   (IV) aqueous animal attractant composition comprising:
      (A) an effective amount of animal attractant perfume containing aninal attractant perfume ingredients and a substantial amount of perfume ingredients that provide a freshness impression to humans;
      (B) optionally, an effective amount of a material selected from the group consisting of: (1) material to inhibit the formation of odor and has at least one attribute selected from the group consisting of: antimicrobial activity, urease inhibition activity, pH adjustment activity, proteolytic activity, and mixtures thereof; (2) odor absorbing material for controlling objectionable odor molecules; and (3) mixtures thereof;
      (C) optionally, solubilizing and/or suspension aid and/ or solvent; and
      (D) aqueous carrier;
   (V) aqueous cleaning composition for animal excretions comprising:
      (A) an effective amount of refreshing perfume containing a substantial amount of perfume ingredients that provide a freshness impression to humans and, optionally, animal repellent perfume ingredients;

(B) an effective amount of cleaning ingredients;

(C) optionally, an effective amount of a material selected from the group consisting of: (1) material to inhibit the formation of odor and has at least one attribute selected from the group consisting of: antimicrobial activity, urease inhibition activity, pH adjustment activity, proteolytic activity, and mixtures thereof; (2) odor absorbing material for controlling objectionable odor molecules; and (3) mixtures thereof;

(D) optionally, solubilizing and/or suspension aid and/or solvent; and (E) aqueous carrier, and (VI) mixtures thereof, said Compositions (II)–(V) optionally being packaged in spray containers, and, optionally, said Compositions (I)–(V) being packaged in association with instructions for using the products to carry out a method of animal control in which either animal litter Composition (I) is used or Composition (II) is used to create animal litter Composition (I); the animal litter Composition (I) is optionally refreshed as needed using Composition (II); different areas are optionally treated with repellent Composition (III) or attractant Composition (IV) to influence the animal to avoid certain areas and/or frequent other areas; and/or, optionally, the cleaning Composition (V) is used for cleaning areas where animal excretions occur and, optionally, to discourage the animal from returning to those areas.

2. A solid liquid-absorbing litter composition, that is useful as animal litter, comprising: (1) solid liquid absorbing litter material; (2) an effective amount of material that inhibits the formation of odor that has at least one attribute selected from the group consisting of antimicrobial activity, urease inhibition activity, pH adjustment activity, proteolytic activity, and mixtures thereof; and also, (3) an effective amount of odor absorbing material for controlling objectionable odor molecules.

3. The composition of claim 2 wherein said solid liquid-absorbing litter material is selected from the group consisting of: minerals; fly ash; absorbing fibrous materials; absorbing webs; absorbing pelletized litter materials; and mixtures thereof.

4. The composition of claim 3 wherein said solid liquid-absorbing litter material is selected from the group consisting of: absorbing fibrous materials; absorbing webs; absorbing pelletized litter materials; and mixtures thereof.

5. The composition of claim 3 wherein said solid liquid-absorbing litter material is mineral selected from the group consisting of: kaolinites, montmorillonites, and bentonites.

6. The composition of claim 2 wherein said liquid-absorbing litter material has the tendency to clump when wetted.

7. The composition of claim 2 wherein said material that inhibits the formation of odor is water soluble metal salt selected from the group consisting of: silver, copper, zinc, ferric, and aluminum salts and mixtures thereof.

8. The composition of claim 7 wherein said material that inhibits the formation of odor is zinc salt.

9. The composition of claim 2 wherein said material that inhibits the formation of odor inhibits or suppresses urease.

10. The composition of claim 2 wherein said material that inhibits the formation of odor is an antimicrobial.

11. The composition of claim 2 wherein said material that inhibits the formation of odor is water-soluble metallic salt selected from the group consisting of water-soluble zinc salts, water-soluble copper salts, and mixtures thereof, present at a level of from about 0.1% to about 10%, by weight of the total composition.

12. The composition of claim 11 wherein said metallic salt is selected from the group consisting of zinc chloride, zinc gluconate, zinc lactate, zinc maleate, zinc salicylate, zinc sulfate, copper chloride, copper gluconate, and mixtures thereof.

13. The composition of claim 12 wherein said metallic salt is $ZnCl_2$.

14. The composition of claim 13 wherein said material that inhibits the formation of odor is at a level of from about 0.001% to about 1% by weight of the litter composition.

15. The composition of claim 14 wherein said material that inhibits the formation of odor is at a level of from about 0.002% to about 0.7%.

16. The composition of claim 2 wherein said odor absorbing material is selected from the group consisting of: cyclodextrin; zeolites; activated carbon; acidic, salt-forming materials; and mixtures thereof.

17. The composition of claim 16 wherein said odor absorbing material is water-soluble cyclodextrin which is selected from the group consisting of: beta-cyclodextrin and its derivatives; alpha-cyclodextrin and its derivatives; gamma-cyclodextrin and its derivatives, and mixtures thereof.

18. The composition of claim 17 wherein said cyclodextrin is beta-cyclodextrin.

19. The composition of claim 18 wherein said odor absorbing material is present at a level of from about 0.2% to about 4%, by weight of the total composition.

20. The composition of claim 16 wherein said odor absorbing material is present at a level of from about 0.3% to about 3%, by weight of the total composition.

21. The composition of claim 19 additionally comprising water-soluble metallic salt selected from the group consisting of water-soluble zinc salts, water-soluble copper salts, and mixtures thereof, present at a level of from about 0.1% to about 10%, by weight of the total composition.

22. The composition of claim 21 wherein said metallic salt is selected from the group consisting of zinc chloride, zinc gluconate, zinc lactate, zinc maleate, zinc salicylate, zinc sulfate, copper chloride, copper gluconate, and mixtures thereof.

23. The composition of claim 22 wherein said metallic salt is $ZnCl_2$ present at a level of from about 0.2% to about 7%, by weight of the total composition.

24. An aqueous freshening composition for animal litter comprising:

(A) an effective amount of refreshing perfume containing a substantial amount of perfume ingredients that provide a freshness impression and which does not contain animal attractant perfume ingredients and contains less than about 25% animal repellent perfume ingredienits, by weight of the refreshing perfume composition;

(B) an effective amount of a material to inhibit the formation of odor and has at least one attribute selected from the group consisting of: urease inhibition activity, pH adjustment activity, proteolytic activity, and mixtures thereof;

(C) optionally, odor absorbing material for controlling objectionable odor molecules;

(D) optionally, solubilizing and/or suspension aid and/or solvent; and (E) aqueous carrier, said composition being packaged in association with instructions to apply it in an effective amount to animal litter and/or surfaces that are affected by animal odors.

25. The composition of claim 24 wherein said perfume is present at a level of from about 0.001% to about 5%, by weight of the total composition.

26. The composition of claim 25 wherein said perfume is present at a level of from about 0.01% to about 1%, by weight of the total composition.

27. The composition of claim 26 wherein said perfume is present at a level of from about 0.05% to about 0.5%, by weight of the total composition.

28. An aqueous animal attractant composition comprising:
(A) an effective amount of animal attractant perfume containing animal attractant perfume ingredients and a substantial amount of perfume ingredients that provide a freshness impression to humans;
(B) optionally, an effective amount of a material selected from the group consisting of: (1) material to inhibit the formation of odor and has at least one attribute selected from the group consisting of: antimicrobial activity, urease inhibition activity, pH adjustment activity, proteolytic activity, and mixtures thereof; (2) odor absorbing material for controlling objectionable odor molecules; and (3) mixtures thereof.

29. The composition of claim 28 wherein said perfume is present at a level of from about 0.01% to about 5%, by weight of the total composition.

30. The composition of claim 29 wherein said perfume is present at a level of from about 0.05% to about 3%, by weight of the total composition.

31. The composition of claim 30 wherein said perfume is present at a level of from about 0.1% to about 2%, by weight of the total composition.

32. The composition of claim 28 wherein said perfume contains from about 0.005% to about 5% of ingredients by weight of the total composition that provide a freshness impression to humans.

33. The composition of claim 32 wherein said perfume contains from about 0.01% to about 3% of ingredients by weight of the total composition that provide a freshness impression to humans.

34. The composition of claim 33 wherein said perfume contains from about 0.05% to about 2% of ingredients by weight of the total composition that provide a freshness impression to humans.

35. The composition of claim 28 wherein the attractant ingredient is selected from the group consisting of nepetalactone, derivatives thereof, and mixtures thereof.

36. The composition of claim 35 wherein the attractant ingredient is nepetalactone.

37. The composition of claim 35 wherein said perfume also contains from about 0.005% to about 5% of ingredients by weight of the total composition that provide a freshness impression to humans.

38. The composition of claim 37 wherein said perfume contains from about 0.01% to about 3% of ingredients that provide a freshness impression to humans.

39. An aqueous animal repellent composition comprising:
(A) an effective amount of repellent perfume containing at least about 40% of repellent perfume ingredients, said repellent perfume ingredients being optionally selected from the group consisting of: methyl salicylate; ethyl salicylate; propyl salicylate; n-butyl salicylate; isobutyl salicylate; iso-amyl salicylate; salicylic aldehyde; cinnamic alcohol; cinnamic aldehyde; menthol; linalool; thymol; cresol; cineol; camphor; citral; terpinene; pinene; limonene; beta-myrcene; muscone; menthone; lemongrass oil; citronella oil; methyl nonyl ketone; methyl phenyl ketone; methyl amyl ketone; methyl nonyl acetaldehyde; leaf aldehyde; pelargonolactone; hinokitiol; kerosene; pyroligneous acid; dodecylbenzene; diphenyl; ethyldiphenyl; diethyldiphenyl; methylnaphthalene; nonylphenyl; dinonylphenol; dodecylphenol; phenylphenol; diphenyl ether; dibenzyl ether; methyl naphthyl ether; bis(2-chloroisopropyl) ether; gamma-alkyl-gamma-butyrolactone; anethole; benzaldehyde; ethyl benzoate; 2-butoxyethanol; nicotine; undecan-2-one; 3-phenylpropenal; and mixtures thereof and, optionally, a substantial amount of non-repellent perfume ingredients that provide a freshness impression, and if the perfume does not contain said non-repellent perfume ingredients, there being at least four repellent perfume ingredients; and
(B) aqueous carrier.

40. The composition of claim 39 wherein said perfume is present at a level of from about 0.01% to about 6%, by weight of the total composition.

41. The composition of claim 40 wherein said perfume is present at a level of from about 0.05% to about 4%, by weight of the total composition.

42. The composition of claim 41 wherein said perfume is present at a level of from about 0.1% to about 2%, by weight of the total composition.

43. The composition of claim 39 wherein said perfume contains at least about 40%, by weight of the perfume composition, of repellent perfume ingredients.

44. The composition of claim 43 wherein said perfume contains at least about 50%, by weight of the perfume composition, of repellent perfume ingredients.

45. The composition of claim 44 wherein said perfume contains at least about 60%, by weight of the perfume composition, of repellent perfume ingredients.

46. The composition of claim 39 wherein said perfume contains at least about 4 different repellent perfume ingredients with no single ingredient being more than about 40% of the total perfume.

47. The composition of claim 46 wherein said perfume contains at least about 5 different repellent perfume ingredients with no single ingredient being more than about 50% of the total perfume.

48. The composition of claim 42 wherein said perfume contains at least about 6 different repellent perfume ingredients.

49. The composition of claim 39 wherein said perfume also contains from about 1% to about 60% of ingredients that provide a freshness impression to humans.

50. The composition of claim 49 wherein said perfume contains from about 5% to about 50% of ingredients that provide a freshness impression to humans.

51. An aqueous cleaning composition for animal excretions comprising:
(A) an effective amount of refreshing perfume containing a substantial amount of perfume ingredients that provide a freshness impression to humans;
(B) an effective amount of cleaning ingredients;
(C) optionally, an effective amount of a mixture of (1) material to inhibit the formation of odor and has at least one attribute selected from the group consisting of antimicrobial activity, urease inhibition activity, pH adjustment activity, and mixtures thereof; and, also optionally, (2) odor absorbing material for controlling objectionable odor molecules;
(D) optionally, solubilizing and/or suspension aid and/or solvent; and (E) aqueous carrier.

52. The composition of claim 51 wherein said perfume is present at a level of from about 0.001% to about 5%, by weight of the total composition.

53. The composition of claim 52 wherein said perfume is present at a level of from about 0.01% to about 1%, by weight of the total composition.

54. The composition of claim 53 wherein said perfume is present at a level of from about 0.05% to about 0.5%, by weight of the total composition.

55. The composition of claim 51 wherein said perfume additionally comprises animal repellent ingredients or animal attractant ingredients.

56. The composition of claim 55 wherein said perfume comprises animal repellent ingredients.

57. The composition of claim 55 wherein said perfume comprises animal attractant ingredients.

58. The composition of claim 51 comprising detergent surfactant.

59. An aqueous composition for reducing malodor impression on animal litter comprising:
(A) an effective amount of refreshing perfume containing a substantial amount of perfume ingredients that provide a freshness impression and which does not contain either repellent perfume ingredients or attractant perfume ingredient;
(B) optionally, an effective amount of a material selected from the group consisting of: (1) material to inhibit the formation of odor and has at least one attribute selected from the group consisting of: antimicrobial activity, urease inhibition activity, pH adjustment activity, proteolytic activity, and mixtures thereof; (2) odor absorbing material for controlling objectionable odor molecules; and (3) mixtures thereof;
(C) optionally, solubilizing and/or suspension aid; and
(D) aqueous carrier, said composition being packaged in association with instructions to apply to litter, or other surfaces having animal odor to reduce the malodor impression.

60. The composition of claim 59 wherein said material to inhibit the formation of odor is at a level of from about 0.01% to about 10% by weight of the total composition and said odor absorbing material is at a level of from about 0.5% to about 10%.

61. The composition of claim 60 wherein said material to inhibit the formation of odor is at a level of from about 0.1% to about 5% by weight of the total composition and said odor absorbing material is at a level of from about 0.1% to about 5%.

62. The composition of claim 61 wherein said material to inhibit the formation of odor is at a level of from about 0.5% to about 2% by weight of the total composition and said odor absorbing material is at a level of from about 0.5% to about 2%.

63. The composition of claim 62 wherein said material to inhibit the formation of odor is selected from water soluble zinc and copper salts and mixtures thereof.

64. The composition of claim 60 wherein said material that inhibits the formation of odor is a urease inhibitor.

65. The composition of claim 60 wherein said odor absorbing material is selected from the group consisting of: cyclodextrin; zeolites; activated carbon; acidic, salt-forming materials; and mixtures thereof.

66. The composition of claim 65 wherein said odor absorbing material is cyclodextrin.

67. The composition of claim 66 wherein said odor absorbing material is water-soluble cyclodextrin which is selected from the group consisting of: beta-cyclodextrin derivatives; alpha-cyclodextrin and its derivatives; gamma-cyclodextrin and its derivatives, and mixtures thereof.

68. The composition of claim 65 wherein said cyclodextrin is beta-cyclodextrin.

69. An aqueous composition for reducing malodor impression on animal litter comprising:
A. from about 0.1% to about 5%. by weight of the total composition, of solubilized, water-soluble, uncomplexed cyclodextrin;
B. from about 0.0001% to about 2% of material that inhibits the formation of odor that has at least one attribute selected from the group consisting of urease inhibition activity, pH adjustment activity, protease activity, and mixtures thereof;
C. optionally from about 0.01% to about 1%, by weight of the total composition of low molecular weight polyols;
D. optionally, but preferably, an effective amount of solubilized, water-soluble, antimicrobial preservative having a water-solubility of greater than about 0.3%;
E. optional perfume; and
F. aqueous carrier; and
said composition being packaged in association with instructions to apply to litter, or other surfaces having animal odor to reduce the malodor impression.

70. The composition according to claim 69 containing from about 80% to about 99% of aqueous carrier.

71. The composition of claim 70 containing from about 85% to about 99% of aqueous carrier.

72. The composition of claim 71 containing from about 90% to about 98% of aqueous carrier.

73. A composition according to claim 1 containing a freshening perfume that contains no effective level of nepetalactone or derivative thereof, or less than about 25% of animal repellent perfume ingredients.

74. A composition according to claim 73 containing a freshening perfume wherein said animal repellent perfume ingredients are selected from the group consisting of: methyl salicylate; ethyl salicylate; propyl salicylate; n-butyl salicylate; isobutyl salicylate; iso-amyl salicylate; salicylic aldehyde; cinnamic alcohol; cinnamic aldehyde; menthol; linalool; thymol; cresol; cineol; camphor; citral; terpinene; pinene; limonene; beta-myrcene; muscone; menthone; lemongrass oil; citronella oil; methyl nonyl ketone; methyl phenyl ketone; methyl amyl ketone; methyl nonyl acetaldehyde; leaf aldehyde; pelargonolactone; hinokitiol; kerosene; pyroligneous acid; dodecylbenzene; diphenyl; ethyidiphenyl; diethyldiphenyl; methyinaphthalene; nonylphenyl; dinonylphenol; dodecylphenol; phenylphenol; diphenyl ether; dibenzyl ether; methyl naphthyl ether; bis(2-chloroisopropyl) ether; gamma-alkyl-gamma-butyrolactone; anethole; benzaldehyde; ethyl benzoate; 2-butoxyethanol; nicotine; undecan-2-one; 3-phenylpropenal; and mixtures thereof.

75. The composition of claim 73 containing an effective amount, sufficient to provide a freshening effect of perfume ingredients selected from the group consisting of: alloocimene; allyl caproate; allyl heptoate; amyl acetate; amyl propionate; anisic aldehyde; anisole; benzyl acetate; benzyl acetone; benzyl alcohol; benzyl butyrate; benzyl formate; benzyl iso valerate; benzyl propionate; beta gamma hexenol; camphene; carvacrol; laevo-carveol; d-carvone; laevo-carvone; cinnamyl formate; cis-3-hexenyl higlate; cis-jasmone; cis-3-hexenyl acetate; citronellol; citronellyl acetate; citronellyl isobutyrate; citronellyl nitrile; citronellyl propionate; cyclohexyl ethyl acetate; cuminic alcohol; cuminic aldehyde; Cyclal C; decyl aldehyde; dihydro myrcenol; dihydromyrcenyl acetate; dimethyl benzyl carbinol; dimethyl benzyl carbinyl acetate; dimethyl octanol; ethyl acetate; ethyl aceto acetate; ethyl amyl ketone; ethyl butyrate; ethyl hexyl ketone; ethyl phenyl acetate; eucalyptol; fenchyl acetate; fenchyl alcohol; tricyclo decenyl acetate; tricyclo decenyl propionate; gamma methyl ionone; gamma-nonalactone; geraniol; geranyl acetate; geranyl formate; geranyl isobutyrate; geranyl nitrile; hexenol; hexenyl acetate; hexenyl isobutyrate; hexyl acetate; hexyl formate; hexyl neopentanoate; hexyl tiglate; hydratropic alcohol; hydroxycitronellal; alpha-ionone; beta-ionone; gamma-ionone; alpha-irone; isoamyl alcohol; isobornyl acetate; isobutyl benzoate; isononyl acetate; isononyl alcohol; isomenthol; isomenthone; para-isopropyl phenylacetaldehyde; isopulegol; isopulegyl acetate; isoquinoline; lauric aldehyde; Ligustral; linalool oxide; linalyl acetate; linalyl formate; methyl acetate; methyl acetophenone; methyl amyl ketone; methyl anthranilate; methyl benzoate; methyl benzyl acetate; methyl chavicol; methyl eugenol; methyl heptenone; methyl heptine carbonate; methyl heptyl ketone; methyl hexyl ketone; methyl phenyl carbinyl acetate; alpha-iso "gamma" methyl ionone; methyl octyl acetaldehyde; nerol; neryl acetate; nonyl acetate; nonyl aldehyde; octalactone; octyl alcohol; octyl aldehyde; para-cymene; para-methyl acetophenone; phenyl acetaldehyde; phenyl ethyl acetate; phenyl ethyl alcohol; phenyl ethyl dimethyl carbinol; phenoxy ethanol; prenyl acetate; propyl butyrate; pulegone; rose oxide; safrole; 4-terpinenol; alpha-terpineol; terpinolene; terpinyl acetate; tetrahydro linalool; tetrahydro myrcenol; tonalid; undecenal; Veratrol; Verdox; vertenex, Viridine; diphenyl methane; gamma-n-methyl ionone; isobutyl quinoline; eugenol; indole; beta-caryophyllene; methyl-n-methyl anthranilate; dodecalactone; lilial (p-t-bucinal); phenyl heptanol; phenyl hexanol; ethyl methyl phenyl glycidate; paramethoxy acetophenone; amyl benzoate; phenoxy ethyl proprionate, heliotropine; and mixtures thereof.

76. The composition according to claim 1 which contains an effective amount of enzyme to inhibit the formation of odor and/or to assist in removing soil.

77. The composition of claim 76 wherein said enzyme is protease and derivatives thereof.

78. The composition of claim 76 wherein said enzyme is present at a level of from about 0.001 mg to about 6 mg of active enzyme per gram of the total composition.

79. An article of manufacture comprising a spray dispenser containing the composition of claim 75.

80. The method of using the article of manufacture of claim 79, in the treatment of articles and/or surfaces with uncomplexed cyclodextrin solution as a level that is effective yet is not discernible when dried on tile surfaces, the method comprising the step of dispensing the composition onto the articles and/or surfaces.

81. The method of preparing the composition of claim 2 wherein the calculated effective amounts of said material that inhibits the formation of odor and said odor absorbing material are dissolved and/or suspended, in appropriate amounts of liquid carrier, enough to sufficiently uniformly distribute the said materials over said solid liquid absorbing litter material.

82. The method of claim 81 wherein the liquid is water and some of the materials have low solubility in water, the water being heated to from about 40° C. to about 90° C. to permit the use of the minimum amount of water.

83. The method of claim 82 wherein said odor absorbing material is uncomplexed cyclodextrin and the composition also contains perfume/cyclodextrin complex, said perfume/cyclodextrin complex and said uncomplexed cyclodextrin being added to the same liquid carrier.

84. A solid liquid-absorbing animal litter composition, comprising a solid liquid absorbing litter material and perfume that contains less than 25% of animal repellent ingredients, or optionally less than 80% of para-cymene, by weight of the perfume headspace.

85. A method for animal care comprising one, or more elements selected from the group consisting of:
  I. a solid liquid-absorbing animal litter composition comprising: (1) a solid liquid absorbing litter material, (2) an effective amount of material that inhibits the formation of odor that has at least one attribute selected from the group consisting of antimicrobial activity, urease inhibition activity, pH adjustment activity, proteolytic activity, and mixtures thereof, and (3) an effective amount of odor absorbing material for controlling objectionable odor molecules;
  II. an aqueous composition for reducing malodor impression on animal litter comprising:
    A. from about 0.1% to about 5%, by weight of the total compositions of solubilized, water-soluble, uncomplexed cyclodextrin;
    B. from about 0.0001% to about 2% of material that inhibits the formation of odor that has at least one attribute selected from the group consisting of urease inhibition activity, pH adjustment activity, proteolytic activity, and mixtures thereof;
    C. optionally, from about 0.01% to about 1%, by weight of the total composition of low molecular weight polyols;
    D. optionally, but preferably, an effective amount of solubilized, water-soluble, antimicrobial preservative having a water-solubility of greater than about 0.3%;
    E. optionally, perfume; and
    F. aqueous carrier;
  III. an aqueous animal repellent composition comprising:
    (A) an effective amount of repellent perfume containing at least about 40% of repellent perfume ingredients and, optionally, a substantial amount of non-repellent perfume ingredients that provide a freshness impression to humans, and if the perfume does not contain said non-repellent perfume ingredients, there being at least four repellent perfume ingredients;
    (B) optionally, an effective amount of a material selected from the group consisting of: (1) material to inhibit the formation of odor and has at least one attribute selected from the group consisting of: antimicrobial activity, urease inhibition activity, pH adjustment activity, proteolytic activity, and mixtures thereof; (2) odor absorbing material for controlliig objectionable odor molecules; and (3) mixtures thereof;
    (C) optionally, solubilizing and/or suspension aid and/or solvent; and
    (D) aqueous carrier;
  IV. an aqueous animal attractant composition comprising:
    (A) an effective amount of attractant perfume containing a substantial amount of perfume ingredients that provide a freshness impression to humans;
    (B) optionally, an effective amount of a material selected from the group consisting of: (1) material to inhibit the formation of odor and has at least one attribute selected from the group consisting of: antimicrobial activity, urease inhibition activity, pH adjustment activity, proteolytic activity, and mixtures thereof; (2) odor absorbing material for controlling objectionable odor molecules; and (3) mixtures thereof;
(C) optionally, solubilizling and/or suspension aid and/or solvent; and
(D) aqueous carrier;

V. an aqueous freshening composition for animal litter comprising:
(A) an effective amount of refreshing perfume containing a substantial amount of perfume ingredients that provide a freshness impression and which does not contain either repellent perfume ingredients or attractant perfume ingredient;
(B) an effective amount of a material to inhibit the formation of odor and has at least one attribute selected from the group consisting of: urease inhibition activity, pH adjustment activity, proteolytic activity, and mixtures thereof;
(C) optionally, odor absorbing material for controlling objectionable odor molecules;
(D) optionally, solubilizing and/or suspension aid and/or solvent; and
(E) aqueous carrier; and VI. an aqueous cleaning composition for animal excretion accidents comprising:
(A) an effective amount of refreshing perfume containing a substantial amount of perfume ingredients that provide a freshness impression to humans, and, optionally, repellent perfume ingredients;
(B) an effective amount of cleaning ingredients;
(C) optionally, an effective amount of a material selected from the group consisting of: (1) material to inhibit the formation of odor and has at least one attribute selected from the group consisting of: antimicrobial activity, urease inhibition activity, pH adjustment activity, proteolytic activity, and mixtures thereof: (2) odor absorbing material for controlling objectionable odor molecules; and (3) mixtures thereof;
(D) optionally, solubilizing and/or suspension aid and/or solvent; and
(E) aqueous carrier;

said compositions optionally being packaged in spray containers, and, optionally, in association with instructions for using the products to carry out a method of animal control in which animal litter Composition I is used or Composition II is used to create animal litter Composition I; the animal litter Composition I is optionally refreshed as needed, using Compositions II and/or V; areas are optionally treated with repellent Composition III or attractant Composition IV products to influence the animals to avoid certain areas and/or frequent other areas; and, optionally, the cleaning Composition VI products are used for cleaning areas where animal excretions occur and thereby discouraging the animal from returning to those areas.

* * * * *